(12) United States Patent
Munoz et al.

(10) Patent No.: US 7,501,091 B2
(45) Date of Patent: Mar. 10, 2009

(54) SENSORS WITH IMPROVED PROPERTIES

(75) Inventors: Beth C. Munoz, Oceanside, CA (US); Kenneth J. Pierce, Aliso Viejo, CA (US); Collin P. Galloway, Nashua, NH (US)

(73) Assignee: Smiths Detection Inc., Pasadena, CA (US)

( * ) Notice: Subject to any disclaimer, the term of this patent is extended or adjusted under 35 U.S.C. 154(b) by 522 days.

(21) Appl. No.: 09/752,656

(22) Filed: Dec. 29, 2000

(65) Prior Publication Data

US 2006/0099715 A1     May 11, 2006

Related U.S. Application Data

(60) Provisional application No. 60/173,964, filed on Dec. 30, 1999.

(51) Int. Cl.
*C12Q 1/68* (2006.01)
*G01N 15/06* (2006.01)
*G01N 27/00* (2006.01)

(52) U.S. Cl. .................. 422/50; 422/68.1; 422/82.01; 422/82.02; 422/83; 422/98; 436/43; 436/151

(58) Field of Classification Search ............ 436/151, 436/43; 422/68.1, 82.01, 82.02, 50, 83, 98; 702/136, 22; 257/414
See application file for complete search history.

(56) References Cited

U.S. PATENT DOCUMENTS 4,970,145 A * 11/1990 Bennetto et al. ....... 204/403.11

(Continued)

FOREIGN PATENT DOCUMENTS

EP     0 950 895 A2     3/1996

FR     2 783 051     9/1998

(Continued)

OTHER PUBLICATIONS

DeQuan Li and B.I. Swanson. Surface Acoustic Wave Thin-Film Chemical Microsensors Based on Covalently Bound C60 Derivatives: A Molecular Self-Assembly Approach. Langmuir 1993, 9, 3341-3344.*

(Continued)

*Primary Examiner*—Brian J Sines
(74) *Attorney, Agent, or Firm*—Foley & Lardner LLP

(57) ABSTRACT

A sensor or a sensor array connected to an electrical measuring apparatus is disclosed. In one embodiment, at least one sensor contains a layer of conductive modified particles which forms an electrical pathway or electrical circuit between two electrodes which are connected to an electrical measuring apparatus. In another embodiment, the first sensor contains at least one region of a nonconducting material and also a region that contains one or more modified particles. The modified particles are preferably conductive. An electrical path exists though the regions of the nonconducting material and the region containing the modified particles. The modified particles are conductive and more preferably are pigment particles such as modified carbon black, wherein the modified particles have attached at least one organic group. Alternatively, or in addition, the modified particle can be an aggregate having a carbon phase and a silicon-containing species phase and/or a metal-containing species phase wherein the aggregate optionally has attached at least one organic group. A sensor array for detecting an analyte in a fluid is also disclosed wherein each sensor emits a different response signature to an analyte wherein at least one of the sensors contains at least the modified particles as described above. Also, the present invention relates to a method for detecting the presence of an analyte in a fluid. The method involves contacting one or more sensors as described above with the analyte to generate a response and detecting the response with a detector that is operatively associated with each sensor in order to detect the presence of an analyte. Other advantages and embodiments are further described.

29 Claims, 4 Drawing Sheets

U.S. PATENT DOCUMENTS

| | | | |
|---|---|---|---|
| 5,256,574 A | 10/1993 | Neuburger et al. | 436/143 |
| 5,554,739 A | 9/1996 | Belmont | 534/885 |
| 5,559,169 A | 9/1996 | Belmont et al. | 523/215 |
| 5,571,311 A | 11/1996 | Belmont et al. | 106/20 R |
| 5,571,401 A | 11/1996 | Lewis et al. | 205/787 |
| 5,575,845 A | 11/1996 | Belmont et al. | 106/712 |
| 5,630,868 A | 5/1997 | Belmont et al. | 106/31.75 |
| 5,672,198 A | 9/1997 | Belmont | 106/20 R |
| 5,698,016 A | 12/1997 | Adams et al. | 106/316 |
| 5,698,089 A | 12/1997 | Lewis et al. | 205/787 |
| 5,707,432 A | 1/1998 | Adams et al. | 106/31.6 |
| 5,713,988 A | 2/1998 | Belmont et al. | 106/31.6 |
| 5,770,028 A * | 6/1998 | Maley et al. | 204/403.11 |
| 5,788,833 A | 8/1998 | Lewis et al. | 205/787 |
| 5,803,959 A | 9/1998 | Johnson et al. | 106/31.75 |
| 5,830,930 A | 11/1998 | Mahmud et al. | 523/215 |
| 5,837,045 A | 11/1998 | Johnson et al. | 106/31.85 |
| 5,851,280 A | 12/1998 | Belmont et al. | 106/472 |
| 5,869,550 A | 2/1999 | Mahmud et al. | 523/215 |
| 5,877,238 A | 3/1999 | Mahmud et al. | 523/215 |
| 5,885,335 A | 3/1999 | Adams et al. | 106/316 |
| 5,891,398 A | 4/1999 | Lewis et al. | 422/82.02 |
| 5,895,522 A | 4/1999 | Belmont et al. | 106/31.6 |
| 5,900,029 A | 5/1999 | Belmont et al. | 8/550 |
| 5,911,872 A | 6/1999 | Lewis et al. | 205/787 |
| 5,916,934 A | 6/1999 | Mahmud et al. | 523/215 |
| 5,919,841 A | 7/1999 | Mahmud et al. | 523/351 |
| 5,922,118 A | 7/1999 | Johnson et al. | 106/31.6 |
| 5,948,835 A | 9/1999 | Mahmud et al. | 523/215 |
| 5,951,846 A | 9/1999 | Lewis et al. | 205/787 |
| 5,955,232 A | 9/1999 | Little et al. | 430/106 |
| 5,959,191 A | 9/1999 | Lewis et al. | 73/31.05 |
| 5,968,243 A | 10/1999 | Belmont et al. | 106/31.65 |
| 5,977,213 A | 11/1999 | Mahmud et al. | 523/215 |
| 6,010,616 A | 1/2000 | Lewis et al. | 205/787 |
| 6,013,229 A | 1/2000 | Lewis et al. | 422/82.02 |
| 6,017,440 A | 1/2000 | Lewis et al. | 205/777.5 |
| 6,017,980 A * | 1/2000 | Wang et al. | 523/215 |
| 6,042,643 A | 3/2000 | Belmont et al. | 106/472 |
| 6,110,994 A | 8/2000 | Cooke et al. | 523/215 |
| 6,221,673 B1 * | 4/2001 | Snow et al. | 436/149 |
| 6,315,956 B1 * | 11/2001 | Foulger | 422/98 |
| 6,438,497 B1 * | 8/2002 | Mansky et al. | 702/22 |
| 6,477,479 B1 * | 11/2002 | Mansky et al. | 702/136 |
| 6,495,892 B2 * | 12/2002 | Goodman et al. | 257/414 |
| 6,528,020 B1 * | 3/2003 | Dai et al. | 422/98 |

FOREIGN PATENT DOCUMENTS

| | | |
|---|---|---|
| GB | 2 226 140 A | 6/1990 |
| WO | WO 96/37547 | 11/1996 |
| WO | WO 97/47691 | 12/1997 |
| WO | WO 98/47971 | 10/1998 |
| WO | WO 99/08105 | 2/1999 |
| WO | WO 99/23174 | 5/1999 |
| WO | WO 99/27357 | 6/1999 |
| WO | WO 99/31175 | 6/1999 |
| WO | WO 99/51690 | 10/1999 |
| WO | WO 99/53300 | 10/1999 |
| WO | WO 99/61902 | 12/1999 |
| WO | WO 99/63007 | 12/1999 |
| WO | WO 00/22051 | 4/2000 |

OTHER PUBLICATIONS

P.M. Ajayan, Nanotubes from Carbon. Chem. Rev. 1999,99 pp. 1787-1799.*

International Search Report for PCT/US00/35626 mailed on Jun. 15, 2001.

Lonergan et al., "Array-Based Vapor Sensing Using Chemically Sensitive, Carbon Black-Polymer Resistors," *Chem. Mater.*, (1996), vol. 8, pp. 2298-2312.

Severin et al., "An Investigation of the Concentration Dependence and Response to Analyte Mixtures of Carbon Black/Insulating Organic Polymer Composite Vapor Detectors," *Anal. Chem.* (Feb. 15, 2000), vol. 72, No. 4, pp. 658-668.

Snow et al., "Size-Induced Metal to Semiconductor Transition in a Stabilized Gold Cluster Ensemble," *Chemistry of Materials*, vol. 10, No. 4, (Apr. 1998), pp. 947-949.

Talik, et al., "Sensing Properties of the CB-PCV Composites for Chlorinated Hydrocarbon Vapours," *Journal of Materials Science*, vol. 27, (1992), pp. 6807-6810.

* cited by examiner

SENSORS WITH IMPROVED PROPERTIES

This application claims the benefit under 35 U.S.C. §119 (e) of prior U.S. Provisional Patent Application No. 60/173,964 filed Dec. 30, 1999, which is incorporated in its entirety by reference herein.

BACKGROUND OF THE INVENTION

In general, the present invention relates to sensors for detecting analytes and electronic nose sensing systems and, in particular, relates to sensors and systems using carbonaceous materials and other particles.

An electronic nose or artificial olfactory system is a device that is capable of detecting a wide variety of analytes in vapors, gases, and liquids. The device contains an array of sensors that in the presence of an analyte produces a response, such as an electrical response. The device produces a unique signature output for a particular analyte. Using pattern recognition algorithms, the output signature can be correlated and compared to a particular analyte or mixture of substances that are known. By comparing the unknown signature with the stored or known signatures the analyte can be identified.

Current commercially available sensors can be used for a variety of applications. These commercial applications include, but are not limited to, environmental toxicology and remediation, biomedicine, such as microorganism classification or detection, material quality control, food and agricultural products monitoring, heavy industrial manufacturing, ambient air monitoring, worker protection, emissions control, and product quality testing.

U.S. Pat. No. 5,571,401, which issued to Lewis et al., and is incorporated herein by reference in its entirety, describes sensors comprising conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and in certain instances 1000 or more sensors. The sensor arrays are useful for the detection of analytes. In certain embodiments, at least one of these sensors comprises a resistor having a plurality of alternating nonconductive regions and conductive regions and as explained therein, gaps exist between the conductive regions and the nonconductive regions. In these sensors, the electrical path length and resistance of a given gap are not constant, but change as the nonconductive region absorbs, adsorbs, or imbibes an analyte. The dynamic aggregate resistance provided by these gaps is, in part, a function of analyte permeation of the nonconductive regions.

The foregoing sensor is based on a conductive network in a nonconductive matrix. The swelling of the nonconductive matrix causes the conductive region to move apart, changing the resistance of the sensor. The change in the resistance of the sensor can be correlated to the concentration of the vapor to be detected. The greater the resistance change for a given level of vapor, the lower the detection limit of the vapor being identified. It is thus advantageous to maximize the resistance change associated with the sensor elements.

For instance, there would be a significant benefit in making sensors which lead to a change in resistance which is greater than conventional sensors. There is a desire, therefore, to improve on one or more components of the conventional sensors in order to achieve this greater sensitivity desired in sensors.

SUMMARY OF THE INVENTION

A feature of the present invention is to provide sensors for detecting an analyte in a fluid which are more sensitive to a variety of different analytes than conventional sensors.

Another feature of the present invention is to provide sensors for detecting an analyte in a fluid, wherein the sensor can avoid the use of a non-conducting polymer.

A further feature of the present invention is to provide sensors for detecting an analyte in a fluid which have a greater resistance change for a given level of vapor emitted by an analyte.

An additional feature of the present invention is to provide sensors for detecting an analyte in a fluid wherein the time of the sensor response is reduced.

An additional feature of the present invention is to provide sensors for detecting an analyte in a fluid wherein the thickness of the sensor can be reduced.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to one or more sensors for detecting an analyte in a fluid. At least one sensor for detecting an analyte in a fluid is electrically connected to an electrical measuring apparatus. The sensor contains a layer of conductive modified particles. In other words, an electrical pathway exists through the layer containing the conductive modified particles. The present invention, in addition, relates to an array of sensors where at least one of the sensors is a sensor electrically connected to an electrical measuring apparatus wherein the sensor contains a layer having conductive modified particles. In this embodiment, the layer containing the conductive modified particles preferably avoids the use of a non-conducting polymer.

The present invention further relates to sensors containing a first and a second sensor electrically connected to an electrical measuring apparatus. The first sensor contains at least one region of a nonconducting material and a region that contains one or more modified particles. An electrical path exists through the regions of the nonconducting material and the region containing the modified particles. The modified particles are conductive and more preferably are pigment particles such as modified carbon black, wherein the carbon black has attached at least one organic group. Alternatively, or in addition, the modified particle can be an aggregate having a carbon phase and a silica-containing species phase and/or a metal-containing species phase wherein the aggregate optionally has attached at least one organic group.

The present invention in addition relates to a sensor array for detecting an analyte in a fluid which involves a series of sensors as described above, wherein each sensor emits a different response signature to an analyte wherein at least one of the sensors contains a region of nonconducting material and a region containing at least a modified particle as described above.

Also, the present invention relates to a method for detecting the presence of an analyte in a fluid. The method involves contacting one or more sensors as described above with the analyte to generate a response and detecting the response with a detector that is operatively associated with each sensor in order to detect the presence of an analyte. The method further involves comparing the response signature to a library of response signatures to determine the particular analyte in the fluid.

It is to be understood that both the foregoing general description and the following detailed description are exemplary and explanatory only and are intended to provide a further explanation of the present invention, as claimed.

The accompanying drawings, which are incorporated in and constitute a part of this invention, illustrate embodiments of the present invention and/or provide data obtained from embodiments of the present invention, and together with the description, serve to explain the principles of the present invention.

DETAILED DESCRIPTION OF THE INVENTION

Figure 4:
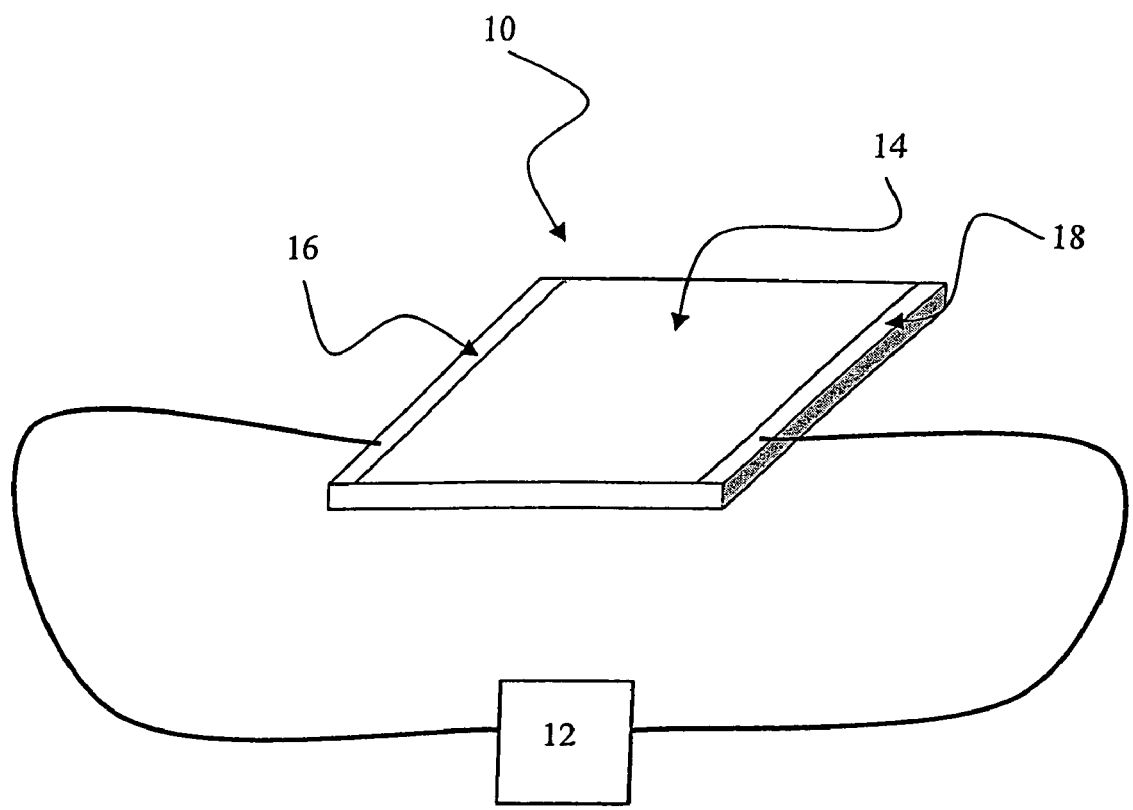
FIG. 4 is a schematic representation of a sensor according to an embodiment of the present invention.

The present invention relates to several embodiments of sensors using one or more types of modified particles which will be further described below. In the first embodiment, as shown schematically in FIG. 4, the present invention relates to one or more sensors for detecting an analyte in a fluid. The sensor 10 is electrically connected to an electrical measuring apparatus 12. The sensor has a layer 14 which contains conductive modified particles. Thus, with the sensor containing conductive modified particles, an electrical path or pathway is formed. In other words, the layer containing the conductive modified particles is located between first and second electrodes 16, 18, respectively to form, essentially an electrical circuit which has a certain resistance as measured by the electrical measuring apparatus. The sensor having the certain preexisting resistance is altered upon the sensor being subjected to an analyte which causes the resistance to be altered due to the presence of the analyte. These changes in resistance can be correlated to the concentration of the analyte detected and/or can be used to create odor signatures which can then be compared with previously recorded and/or stored response signatures. Upon comparing the odor signature of the analyte detected with previously recorded and/or stored response signatures, a match can be made with a library of odor signatures previously recorded in order to determine the concentration and/or identification of the analyte. In this embodiment, the presence of a nonconducting material as in previous sensors is not necessary and preferably is not used. The sensor containing the layer of conductive modified particles is sufficient for the sensor to sense the analyte and determine its concentration and/or odor signature. Thus, the sensor in this embodiment is simpler in design and more economical to manufacture. In addition, the sensor in this embodiment is easier to produce from the stand point that only a dispersion of modified particles needs to be applied onto a substrate, for instance, in order to form a sensor for purposes of the present invention. The layer containing the conductive modified particles can optionally contain other conducting materials as well as nonconducting materials. Examples of other conducting materials and/or nonconducting materials are described below. In addition, the modified particles are described in significant detail below as well. The description that follows with regard to the modified particles can be used in any of the embodiments described in the present invention.

Figure 5:
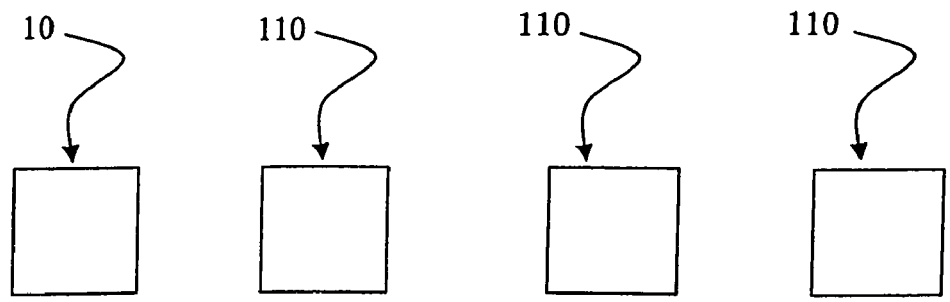
FIG. 5 is a schematic representation of a sensor array according to an embodiment of the present invention.

An array of sensors can also be used in this embodiment for detecting an analyte in the fluid, as shown schematically in FIG. 5. At least one of the sensors 10 contains a layer having the conductive modified particles. The other sensors, shown as an additional sensors 110 can also use the same design, in other words, also contain a layer of conductive modified particles or can use sensors having conventional designs, for instance, like the ones described in U.S. Pat. Nos. 5,571,401 and 5,788,833 which are both incorporated in their entirety by reference herein. Typically, the amount of conductive modified particles which are used to form a layer for the sensor of the present invention is an amount sufficient to form an electrical pathway between the two electrodes forming a part of the sensor. For purposes of the present invention, an amount above this amount can also be used if desired.

In more detail, the sensors of the present invention used, for instance, to detect an analyte in a fluid, contain a first sensor and a second sensor. Both sensors are electrically connected to an electrical measuring apparatus. The first sensor contains a region of nonconducting material and a region of conducting material. Also, an electrical path exists through the regions of nonconducting material and the regions of the conducting material. These sensors have a certain preexisting resistance which is altered upon the sensor being subjected to an analyte which causes a portion of the sensor to swell leading to a change in resistance. In a preferred embodiment, the nonconductive region swells due to the presence of the analyte causing the conductive region to move apart, changing the resistance of the sensor. These changes in resistance can be correlated to the concentration of the analyte detected and further can be used to create odor signatures which can then be compared with previously recorded and/or stored response signatures. Means to compare the response signature or odor signature with the library of signatures recorded and/or stored previously can then be used to match the odor signature to determine the concentration and/or identification of the analyte.

With respect to the nonconducting regions, these regions contain nonconducting materials. For instance, the nonconducting materials can be polymeric and include, but are not limited to, main-chain carbon polymers, main-chain acyclic heteroatom polymers, and main-chain heterocyclic polymers. The nonconducting materials can be one polymer or a combination of two or more polymers with other optional ingredients possible, such as plasticizers and other conventional ingredients commonly associated with the formation of polymeric articles. Examples of various polymers include, but are not limited to, poly(dienes); poly(alkenes); poly(acrylics); poly(methacrylics); poly(vinyl ethers); poly(vinyl thioethers); poly(vinyl alcohols); poly(vinyl ketones); poly(vinyl halides); poly(vinyl nitriles); poly(vinyl esters); poly(styrenes); poly(arylenes); poly(oxides); poly(carbonates); poly(esters); poly(anhydrides); poly(urethanes); poly(sulfonates); poly(siloxanes); poly(sulfides); poly(thioesters); poly(sulfones); poly(sulfonamides); poly(amides); poly(urens); poly(phosphazenes); poly(silanes); poly(silazanes); poly(furan tetracarboxylic acid diimides); poly(benzoxazoles); poly(oxadiazoles); poly(benzothiazinophenothiazines); poly(benzothiazoles); poly(pyrazinoquinoxalines); poly(pyromenitimides); poly(quinoxalines); poly(benzimidazoles); poly(oxindoles); poly(oxoisoindolines); poly(dioxoisoindalines); poly(triazines); poly(pyridazines); poly(piperazines); poly(pyridines); poly(piperidines); poly(triazoles); poly(pyrazoles); poly(pyrrolidines); poly(carboranes); poly(oxabicyclononanes); poly(dibenzofurans); poly(phthalides); poly(acetals); poly(anhydrides); carbohydrates, and the like.

With respect to the conducting region, preferably, the conducting region contains one or more modified particles. The conducting region can include other conducting materials and/or nonconducting materials. Examples of other conducting materials include organic conductors such as conducting polymers; inorganic conductors such as metal and metal alloys; and mixed inorganic/organic conductors such as tetracyano platinate complexes, and the like. Examples of other types of conducting materials are set forth in U.S. Pat. Nos. 5,571,401 and 5,788,833 both incorporated herein in their entireties by reference.

For purposes of the present invention, the modified particles are preferably conductive particles having at least one organic group attached to the particles. Preferably, the particle is a conductive pigment particle. The pigment can be any wide range of colors. The particles can be any size such as from about 100 microns or more to less than one micron and preferably have a size range of from about 0.05 microns to about 25 microns.

The pigment can be, but is not limited to, pigments traditionally used in ink compositions (including inkjet ink compositions), coating compositions (including paint formulations), liquid and solid toners, films, plastics, rubbers, and the like. Examples include, but are not limited to, black pigments (e.g., carbon products like carbon black) and other colored pigments (e.g., polymeric and organic pigments). Carbon black is preferred. Various commercial grades exist having varying particle size and structure, pH, channel content, surface area, amount of chain-like structure, volatile content, coarsens, each produced through minute adjustments in different reactors. Carbon black is commercially available from Cabot Corporation, Boston, Mass. The surface modified carbon blacks and other pigments can be specifically tailored to exhibit a variety of characteristics. Various characteristics include, but are not limited to, its ability to absorb ultraviolet light, polarity, conductivity, size, permeability, solubility, dispersability, crosslinkability, temperature coefficient, interaction with other polymers, sensor hysteresis, vapor discrimination, etc. Thus, the surface of the carbon black or other particles can be modified with a variety of functional groups in order to deliver a specific sensor characteristic. Special performance characteristics can be obtained depending on the specific surface modification employed.

The pigment may be chosen from a wide range of conventional pigments. For instance, the pigment product can be any carbon product capable of reacting with a diazonium salt to form the modified pigment product. The carbon may be of the crystalline or amorphous type. Examples include, but are not limited to, graphite, carbon black, vitreous carbon, activated charcoal, activated carbon, carbon fibers, and mixtures thereof. Finely divided forms of the above are preferred. It is also possible to utilize mixtures of different pigment products.

The colored pigment can be blue, black, brown, cyan, green, white, violet, magenta, red, yellow, as well as mixtures thereof. Suitable classes of colored pigments include, for example, carbon black, carbon products, anthraquinones, phthalocyanine blues, phthalocyanine greens, diazos, monoazos, pyranthrones, perylenes, heterocyclic yellows, quinacridones, and (thio)indigoids. Representative examples of phthalocyanine blues include copper phthalocyanine blue and derivatives thereof (Pigment Blue 15). Representative examples of quinacridones include Pigment Orange 48, Pigment Orange 49, Pigment Red 122, Pigment Red 192, Pigment Red 202, Pigment Red 206, Pigment Red 207, Pigment Red 209, Pigment Violet 19 and Pigment Violet 42. Representative examples of anthraquinones include Pigment Red 43, Pigment Red 194 (Perinone Red), Pigment Red 216 (Brominated Pyanthrone Red) and Pigment Red 226 (Pyranthrone Red). Representative examples of perylenes include Pigment Red 123 (Vermillion), Pigment Red 149 (Scarlet), Pigment Red 179 (Maroon), Pigment Red 190 (Red), Pigment Violet 19, Pigment Red 189 (Yellow Shade Red) and Pigment Red 224. Representative examples of thioindigoids include Pigment Red 86, Pigment Red 87, Pigment Red 88, Pigment Red 181, Pigment Red 198, Pigment Violet 36, and Pigment Violet 38. Representative examples of heterocyclic yellows include Pigment Yellow 1, Pigment Yellow 3, Pigment Yellow 12, Pigment Yellow 13, Pigment Yellow 14, Pigment Yellow 17, Pigment Yellow 65, Pigment Yellow 73, Pigment Yellow 74, Pigment Yellow 151, Pigment Yellow 117, Pigment Yellow 128 and Pigment Yellow 138. Such pigments are commercially available in either powder or press cake form from a number of sources including, BASF Corporation, Engelhard Corporation and Sun Chemical Corporation. Examples of other suitable colored pigments are described in the Colour Index, 3rd edition (The Society of Dyers and Colourists, 1982). The color pigment will typically have a wide range of BET surface areas, as measured by nitrogen adsorption.

Other examples of particles include, but are not limited to, carbonaceous materials obtained by the pyrolysis of cellulosic, fuel oil, polymeric, or other precursors, carbon cloth, carbon aerogels, pyrolized ion exchange resins, pyrolized polymer resins, mesoporous carbon microbeads, pelleted carbon powder, nanotubes, buckyballs, densified carbon black, carbon clad materials, such as carbon clad silica, and combinations thereof or activated versions thereof. The carbonaceous material can also be a waste product or by-product of carbonaceous material obtained by pyrolysis. Commercial examples of carbon black include, but are not limited to, Black Pearls® 2000 carbon black, Black Pearls® 430 carbon black, Black Pearls® 900 carbon black, and Black Pearls® 120 carbon black, all available from Cabot Corporation.

Also, for purposes of the present invention, the modified particle can be an aggregate comprising a carbon phase and a silicon-containing species phase and optionally having attached at least one organic group. A description of this aggregate as well as means of making this aggregate is described in PCT Publication No. WO 96/37547 and WO 98/47971 as well as U.S. Pat. Nos. 5,830,930; 5,869,550; 5,877,238; 5,919,841; 5,948,835; and 5,977,213. All of these patents and publications are hereby incorporated in their entireties herein by reference.

The modified particle for purposes of the present invention, can also be an aggregate comprising a carbon phase and metal-containing species phase where the metal-containing species phase can be a variety of different metals such as magnesium, calcium, titanium, vanadium, cobalt, nickel, zirconium, tin, antimony, chromium, neodymium, lead, tellurium, barium, cesium, iron, molybdenum, aluminum, and zinc, and mixtures thereof, and optionally having attached at least one organic group. The aggregate comprising the carbon phase and a metal-containing species phase is described in U.S. Pat. No. 6,017,980, also hereby incorporated in its entirety herein by reference.

Also, for purposes of the present invention, the modified particle can be at least a partially silica-coated carbon black, such as that described in U.S. Pat. No. 5,916,934 and PCT Publication No. WO 96/37547, published Nov. 28, 1996, also hereby incorporated in their entirety herein by reference. The silica-coated carbon black can also optionally have at least one organic group.

With respect to the particle size of the pigments, the particle size distribution is based on the mean volume diameter of the pigment particles as measured by the dynamic light scattering method. The particle size distribution range can be from about 10 nm to about 1 micron, and preferably is from about 10 nm to about 500 nm, more preferably is from about 20 nm to about 300 nm, and most preferably is from about 50 nm to about 200 nm.

As indicated above, the modified particle is preferably a pigment having attached at least one organic group. The organic group preferably contains at least one aromatic group, at least one $C_1$-$C_{100}$ alkyl group, or mixtures thereof. Preferably, the groups attached to the particles are crosslinkable chemical groups. For instance, the modified particles can be suspended in a solvent, deposited on a sensor substrate and subsequently crosslinked to enhance sensor stability.

At least one aromatic group includes, but is not limited to, unsaturated cyclic hydrocarbons containing one or more rings and may be substituted or unsubstituted, for example with alkyl groups. Aromatic groups include aryl groups (for example, phenyl, naphthyl, anthracenyl, and the like) and heteroaryl groups (for example, imidazolyl, pyrazolyl, pyridinyl, thienyl, thiazolyl, furyl, triazinyl, indolyl, and the like). At least one $C_1$-$C_{100}$alkyl group may be branched or unbranched, substituted or unsubstituted.

The modified particles can include at least one ionic group, ionizable group, or both as part of the organic group. An ionizable group is one capable of forming an ionic group in the medium of use. The ionic group may be an anionic group or a cationic group and the ionizable group may form an anion or cation. Ionizable functional groups forming anions or anionic groups include, for example, acidic groups. Ionic groups include salts of acidic groups. The organic groups, therefore, include groups derived from organic acids. Preferably, when an organic group contains an ionizable group forming an anion, an anionic group, or a mixture, such an organic group has a) an aromatic group or a $C_1$-$C_{100}$ alkyl group and b) at least one acidic group having a p$K_a$ of less than 11, or at least one salt of an acidic group having a p$K_a$ of less than 11, or a mixture of at least one acidic group having a p$K_a$ of less than 11 and at least one salt of an acidic group having a p$K_a$ of less than 11. The p$K_a$ of the acidic group refers to the p$K_a$ of the organic group as a whole, not just the acidic substituent. More preferably, the p$K_a$ is less than 10 and most preferably less than 9. Preferably, the aromatic group or the alkyl group of the organic group is directly attached to the particle, e.g., pigment. The aromatic group may be further substituted or unsubstituted, for example, with alkyl groups. More preferably, the organic group is a phenyl or a naphthyl group and the acidic group is a sulfonic acid group, a sulfinic acid group, a phosphonic acid group, or a carboxylic acid group. Most preferably, the organic group is a substituted or unsubstituted sulfophenyl group or a salt thereof; a substituted or unsubstituted carboxyphenyl group or salt thereof; a substituted or unsubstituted (polysulfo)phenyl group or a salt thereof; a substituted or unsubstituted sulfonaphthyl group or a salt thereof; or a substituted or unsubstituted (polysulfo)naphthyl group or a salt thereof.

Specific organic groups having an ionizable functional group forming an anion are p-sulfophenyl, 4-hydroxy-3-sulfophenyl, and 2-sulfoethyl. Other organic groups having ionizable functional groups forming anions can also be used.

Examples of organic groups that are anionic in nature include, but are not limited to, $-C_6H_4-COO^-X^+$; $-C_6H_4-SO_3^-X^+$; $-C_6H_4-(PO_3)^{-2}2X^+$; $-C_6H_2-(COO^-X^+)_3$; $-C_6H_3-(COO^-X^+)_2$; $-(CH_2)_z-(COO^-X^+)$; $-C_6H_4-(CH_2)_z-(COO^-X^+)$, wherein $X^+$ is any cation such as $Na^+$, $H^+$, $K^+$, $NH_4^+$, $Li^+$, $Ca^{2+}$, $Mg^{2+}$ and the like and z is an integer from 1 to 18. As recognized by those skilled in the art, $X^+$ may be formed in-situ as part of the manufacturing process or may be associated with the aromatic or alkyl group through a typical salt swap or ion-exchange process.

Amines represent examples of ionizable functional groups that form cations or cationic groups and may be attached to the same types of groups as discussed above for the ionizable groups which form anions. For example, amines may be protonated to form ammonium groups in acidic media. Preferably, an organic group having an amine substituent has a p$K_b$ of less than 5. Quaternary ammonium groups ($-NR_3^+$), quaternary phosphonium groups ($-PR_3^+$) and sulfonium groups ($-SR_2^+$) also represent examples of cationic groups. Preferably, the organic group contains an aromatic group such as a phenyl or a naphthyl group and a quaternary ammonium or a quaternary phosphonium or sulfonium group. Quaternized cyclic amines, and even quaternized aromatic amines, can also be used as the organic group. Thus, N-substituted pyridinium compounds, such as N-methyl-pyridyl, can be used in this regard.

Examples of organic groups that are cationic in nature include, but are not limited to, $-C_6H_4N(CH_3)_3^+Y^-$, $-C_6H_4COCH_2N(CH_3)_3^+Y^-$, $-C_6H_4(NC_5H_5)^+Y^-$, $-(C_5H_4N)C_2H_5^+Y$, $-C_6H_4COCH_2(NC_5H_5)^+Y^-$, $-(C_5H_4N)CH_3^+Y^-$, and $-C_6H_4CH_2N(CH_3)_3^+Y^-$, wherein $Y^-$ is any halide or an anion such as $NO_3^-$, $OH^-$, $CH_3COO^-$ and the like; or combinations thereof. As recognized by those skilled in the art, $Y^-$ may be formed in-situ as part of the manufacturing process or may be associated with the aromatic or alkyl group through a typical salt swap or ion-exchange process.

Further examples of representative organic groups and methods of attachment are also described in U.S. Pat. Nos. 5,554,739; 5,559,169; 5,571,311; 5,575,845; 5,630,868; 5,672,198; 5,698,016; 5,837,045; 5,922,118; 5,968,243; 6,042,643; 5,900,029; 5,955,232; 5,895,522; 5,885,335; 5,851,280; 5,803,959; 5,713,988; 5,707,432; and 6,110,994; and International Patent Publication Nos. WO 97/47691; WO 99/23174; WO 99/31175; WO 99/51690; WO 99/63007; and WO 00/22051; all hereby incorporated in their entirety by reference herein. The groups and methods of attachments described in International Published Application Nos. WO 99/23174 and WO 99/63007, can also be used and are incorporated in their entirety by reference herein.

Advantageously, the modified particles used in the present invention are easy to disperse in a wide variety of solvents. Suitable surface modifications include, but are not limited to, covalent attachment, noncovalent attachment and electrostatic attachment of functional groups or ligands to the particles. The modification of the particles can involve functional groups of various polarities, molecular sizes, functionality, reactive groups, and dispersibilities. Groups that can be attached include, but are not limited to, polymers, alkanes, alkenes, alkynes, dienes, alicyclic hydrocarbons, arenes, heterocyclics, alcohols, ethers, ketones, aldehydes, carbonyls, carbanions, polynuclear aromatics and derivatives of such organics, functional groups, chiral groups, polyethylene glycol, surfactants, detergents, biomolecules, polysaccharides, protein complexes, polypeptides, dendrimeric materials, oligonucleotides, fluorescent moieties and radioactive groups.

In certain instances, the sensors containing the modified particles are covalently modified to have more than one attached group or mixtures thereof.

Additional examples of organic groups that can be attached include, but are not limited to, alkyl groups, 18-carbon alkyl groups, 4-carbon alkyl groups, alkyl esters, oligoethers, and anionic groups. Additional modifications include, but are not limited to, poly(chloromethylstyrene), poly(alkylacrylate), alkyl esters and anionic groups. The foregoing ligands include isomers, diasteromers, chiral groups, racemic modifications, and other modifications.

Chemical moieties suitable to use to modify the ligands include, but are not limited to, alkyl, bromo, chloro, iodo, fluoro, amino, hydroxyl, thio, phosphino, alkylthio, cyano, nitro, amido, carboxyl, aryl, heterocyclyl, ferrocenyl, or heteroaryl. The ligands can be attached to the particle, such as carbon black, by various methods including, but not limited to, covalent attachment and electrostatic attachment.

Further examples of the ionic or ionizable groups are amphiphilic counterions, which may be cationic or anionic in nature. An amphiphilic counterion is a molecule or compound typically described as having a hydrophilic polar "head" and a hydrophobic "tail." Representative examples of cationic and anionic amphiphilic counterions include those set forth and described in U.S. Pat. No. 5,698,016 to Adams et al., the entire description of which is incorporated herein by reference.

For purposes of further illustrating the present invention, an amphiphilic counterion can be used. The modified pigment, as described herein, preferably has a cationic functionality (i.e. positive charge) or anionic functionality (negative charge). The charge preferably is created by the ionic or ionizable group of the aromatic group or $C_1$-$C_{100}$ alkyl group attached to the pigment. If the organic group of the modified pigment is anionic in nature, then the amphiphilic counterion will be cationic or positive charging. Similarly, if the organic group of the modified pigment is cationic in nature, then the amphiphilic counterion will be anionic or negative charging. Examples of cationic amphiphilic counterions include, but are not limited to, those described ammonium ions that may be formed from adding acids to the following: a fatty amine, an ester of an amino alcohol, an alkylamine, a polymer containing an amine functionality, a polyethoxylated amine, a polypropoxylated amine, a polyethoxylated polypropoxylated amine, an aniline and derivatives thereof, a fatty alcohol ester of amino acid, a polyamine N-alkylated with a dialkyl succinate ester, a heterocyclic amine, a guanidine derived from a fatty amine, a guanidine derived from an alkylamine, a guanidine derived from an arylamine, an amidine derived from a fatty amine, an amidine derived from a fatty acid, an amidine derived from an alkylamine, or an amidine derived from an arylamine. The pKa of the ammonium ion is preferably greater than the pKa of the protonated form of the aromatic or alkyl group on the pigment.

Specific examples of cationic amphiphilic ions include dioctylammonium, oleylammonium, stearylammonium, dodecylammonium, dimethyldodecylammonium, stearylguanidinium, oleylguanidinium, soyalkylammonium, cocoalkylammonium, oleylammoniumethoxylate, protonated diethanolaminedimyristate, and N-oleyldimethylammonium. Generally, to form the ammonium ions described above, the various compounds described above such as fatty amines, esters of amino alcohols, etc., are reacted with an acid such as carboxylic acid, a mineral acid, an alkyl sulfonic acid, or an aryl sulfonic acid.

Quaternary ammonium salts can also be used as the sources of the cationic amphiphilic ion. Examples include, but are not limited to, a fatty alkyl trimethyl ammonium, a di(fatty alkyl)dimethylammonium, an alkyl trimethyl ammonium, or 1-alkyl pyridinium salt, where the counterion is a halide, methosulfate, sulfonate, a sulfate or the like. Also, phosphonium salts, such as tetraphenylphosphonium chloride can be used as the sources of the amphiphilic ion.

Cationic amphiphilic ions for use in the present invention include those represented by the formula $R_4N^+$, wherein R is independently hydrogen, $C_1$-$C_{30}$ alkyl, $C_1$-$C_{30}$ alkenyl, $C_7$-$C_{30}$ aralkyl, and $C_7$-$C_{30}$ alkaryl. Another example of a suitable amphiphilic ion is a polymer containing an ammonium ion derived from an amine containing polymer. The amine containing polymer can be a copolymer of an amine containing monomer, such as dimethylaminoethyl methacrylate or acrylate, or vinylpyridine or vinylimidazole, and another monomer such as methyl acrylate, methyl methacrylate, butyl acrylate, styrene, and the like. The polymer may also be a polyethyleneimine (PEI), derivatized or acylated PEI, polyallylamine, or polydiallylamine. The polymer may also be a ter- or tetra-polymer containing a mixture of an amine containing monomer and two or three other amine containing monomers, respectively. Such a polymer may be prepared by any means, such as radical (emulsion, suspension, or solution) or anionic polymerization, stable free radical polymerization or atom transfer polymerization.

As stated earlier, the amphiphilic counterion can alternatively be an anionic amphiphilic counterion. Examples of such anionic amphiphilic ions include, but are not limited to, an alkylbenzene sulfonate, an alkyl sulfonate, an alkylsulfate, a sulfosuccinate, a sarcosine, an alcohol ethoxylate sulfate, an alcohol ethoxylate sulfonate, an alkyl phosphate, an alkylethoxylated phosphate, an ethoxylated alkylphenol sulfate, a fatty carboxylate, a taurate, an isethionate, an aliphatic carboxylate, or an ion derived from a polymer containing an acid group. Sources of specific and preferred examples of anionic amphiphilic ions include, but are not limited to, sodium dodecylbenzene sulfonate, a sodium dodecylsulfate, Aerosol OT, an oleic acid salt, a ricinoleic acid salt, a myrisitic acid salt, a caproic acid salt, sodium 2-octyldodecanoate, sodium bis(2-ethylhexyl)sulfosuccinate, a sulfonated polystyrene, or homo- or copolymers of acrylic acid or methacrylic acid or salts thereof.

Generally, the above-identified amphiphilic counterions and related compounds are commercially available in salt form or can be routinely made by one of ordinary skill in the art.

Other examples of organic groups that can be attached to the pigment or particle include groups with the following formulas. In each of the following formulas, —X is attached directly to the pigment and —X' can be directly attached to the pigment. Each of the following organic groups, for purposes of the present invention, can optionally contain an ionic group, an ionizable group, or both.

A further example of a modified pigment is a pigment having attached at least one group comprising the formula:

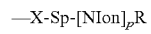

—X-Sp-[NIon]$_p$R wherein X represents an aromatic group or an alkyl group, NIon represents at least one non-ionic group, Sp represents a spacer group, R represents hydrogen, an aromatic group, or an alkyl group, and p is an integer of from 1 to 500.

The aromatic group with respect to the X substituent and/or the R substituent can be substituted or unsubstituted and can be, for instance, an aryl or heteroaryl group. The aromatic group can be substituted with any group, such as one or more alkyl groups or aryl groups. Preferably, the aromatic group is a phenyl, naphthyl, anthracenyl, phenanthrenyl, biphenyl, pyridinyl, benzothiadiazolyl, or benzothiazolyl. Examples of the alkyl group with respect to the X substituent and/or the R substituent include, but are not limited to, substituted or unsubstituted alkyl groups which may be branched or unbranched. The alkyl group can be substituted with one or more groups, such as aromatic groups. Preferred examples of the alkyl group for purposes of the X substituent include, but are not limited to, $C_1$-$C_{12}$, like methyl, ethyl, propyl, butyl, pentyl, or hexyl groups. In other words, X and/or R can represent a branched or unbranched, substituted or unsubstituted, saturated or unsaturated hydrocarbon. Examples of substituted groups include, but are not limited to, an ester group, an amide group, an ether group, a carboxyl group, an aryl group, an alkyl group, and the like.

Sp or the spacer group as used herein is a link between two groups and can be a bond, or a chemical group such as, but not limited to, $CO_2$, $SO_2CH_2CH_2$, $CH_2CH_2$, $CHR"CH_2CH_2CHR"$, $CHR"$, $O_2C$, $SO_2$, $CO$, $SO_3$, $OSO_2$, $SO_3NR"$, $R"NSO_2$, $NHCO$, $CONR"$, $NR"CO_2$, $O_2CNR"$, $NR"CONR"$, $O,S$, $NR"$, $SO_2C_2H_4$, arylene, alkylene, $NR"CO$, $NHCO_2$, $O_2CNH$, $NCHONH$, and the like, wherein R", which can be the same or different, represents an organic group such as a substituted or unsubstituted aryl and/or alkyl group.

Examples of the non-ionic group include, but are not limited to, groups having no apparent ionic charge, such as polymers of ethylene oxide, propylene oxide, other alkylene oxides, carboxylic acid esters, glycols, alcohols, esters, alkanolamine-fatty acid condensates, silicones, isocyanates, alkylpyrrolidenes, and alkylpolyglycosides. In non-aqueous media, the non-ionic group, in addition to the aforementioned groups, may have carboxylates, sulfonates, phosphates, amines, and other groups that typically demonstrate an ionic nature in water. The non-ionic group is preferably a $C_1$-$C_{12}$ alkyl group, or a $C_1$-$C_{12}$ alkylene oxide group. p can be 1-25, 26-50, 51-75, 75-100, and/or 101-500, and p preferably is 5 to 50.

The X substituent and/or non-ionic group may be substituted with one or more functional groups. The functional group preferably contains a lypophilic group. Examples of functional groups include, but are not limited to, R', OR', COR', COOR', OCOR', carboxylates, halogens, CN, $NR'_2$, $SO_3H$, sulfonates, $-OSO_3-$, $NR'(COR')$, $CONR'_2$, $NO_2$, $PO_3H_2$, phosphonates, phosphates, $N=NR'$, SOR', $NSO_2R'$, wherein R' which can be the same or different, is independently hydrogen, branched or unbranched $C_1$-$C_{20}$ substituted or unsubstituted, saturated or unsaturated hydrocarbons, e.g., alkyl, alkenyl, alkynyl, substituted or unsubstituted aryl, substituted or unsubstituted heteroaryl, substituted or unsubstituted alkylaryl, or substituted or unsubstituted arylalkyl.

Amines also represent examples of functional groups as well as quaternary ammonium groups ($-NR_3^+$) and quaternary phosphonium groups ($-PR_3^+$), as well as quaternary sulfonium groups ($-SR_2^+$).

In an additional embodiment of the present invention, the modified pigment can be a pigment having attached at least one group comprising the formula:

—X-Sp-[A]$_p$R wherein X represents an aromatic group or an alkyl group; Sp represents a spacer group; A represents an alkylene oxide group of from about 1 to about 12 carbons; p represents an integer of from 1 to 500, and R represents hydrogen, a substituted or unsubstituted alkyl group, or a substituted or unsubstituted aromatic group. A can be the same or different when p is greater than 1. X can be substituted or unsubstituted and can include substituted groups such as an ester group, an amide group, an ether group, a carbonyl group, an aryl group, an alkyl group and the like. The substituted groups can be attached or linked to A.

Examples of preferred alkylene groups include, but are not limited to, $-CH_2-CH_2-O-$; $-CH(CH_3)-CH_2-O-$; $-CH_2CH_2CH_2-O-$; $-CH_2CHCH_3-O-$; or combinations thereof.

In another embodiment of the present invention, the modified pigment can be a pigment having attached at least one group comprising the formula:

—X-Sp-[(—CH$_2$)$_m$—O—)$_p$—R]

wherein X is described above, and for instance can represent an aromatic group or an alkyl group as described earlier, m is an integer of from 1 to 12, preferably 2 or 3, p is an integer of from 1 to 500, Sp represents a spacer group, and R is described above, and for instance can be hydrogen, a substituted or unsubstituted alkyl group, or a substituted or unsubstituted aromatic group. Examples of R substituents include, but are not limited to, hydrogen, methyl, ethyl, butyl, or propyl groups. p can be 1-25, 26-50, 51-75, 76-100, and 101-500, and is preferably 5 to 50. Particularly preferred groups of this formula are where X is a phenylene group, m is 1 to 5, and more preferably 2 or 3, p is 5 to 50, more preferably 44-45, and R is hydrogen or a methyl group. Another preferred group is where m is 2, p is 7, R is a methyl group, and X is a phenylene group.

In yet another embodiment of the present invention, the modified pigment can be a pigment having attached at least one polymeric group, wherein the polymeric group comprises the formula:

—X-Sp-[polymer]R wherein X and Sp are described above, and for instance can represent at least an aromatic group or at least an alkyl group as described earlier, "polymer" represents a polymeric group comprising repeating monomer groups or multiple monomer groups or both, optionally having at least one —X' group. The group "polymer" can be substituted or unsubstituted with additional groups. R is described above and for instance can represent hydrogen, a bond, a substituted or unsubstituted alkyl group, or a substituted or unsubstituted aromatic group. X' represents an aromatic group or alkyl group, and each X' and X can be the same or different. The total monomer repeating units that comprise the group "polymer" is not greater than about 5,000 monomer repeating units. X and/or X' can be substituted or unsubstituted and can include substituted groups such as an ester group, an amide group, an ether group, and the like. The substituted groups can be linked to the group "polymer." Also, when R represents a bond, the available bond can be attached to the pigment. The polymeric group can be any polymeric group capable of being attached to a pigment.

For purposes of the present invention and this formula immediately above, one or more polymeric groups that comprise the group "polymer" can be present. The polymeric group can be a thermoplastic polymeric group or a thermosetting polymeric group. Further, the polymeric group can be a homopolymer, copolymer, terpolymer, and/or a polymer containing any number of different repeating units. Further, the polymeric group present in the present invention can be any type of polymeric group, such as a random polymer, alternating polymer, graft polymer, block polymer, star-like polymer, and/or comb-like polymer. The polymeric group used in the present invention can also be one or more polyblends. The polymeric group can be an interpenetrating polymer network (IPN); simultaneous interpenetrating polymer network (SIN); or interpenetrating elastomeric network (IEN).

Specific examples of polymeric groups include, but are not limited to, linear-high polymers such as polyethylene, poly (vinylchloride), polyisobutylene, polystyrene, polycaprolactam (nylon), polyisoprene, and the like. Other general classes of polymeric groups of the present invention are polyamides, polycarbonates, polyelectrolytes, polyesters, polyethers, (polyhydroxy)benzenes, polyimides, polymers containing sulfur (such as polysulfides, (polyphenylene)sulfide, and polysulfones), polyolefins, polymethylbenzenes, polystyrene and styrene copolymers (ABS included), acetal polymers, acrylic polymers, acrylonitrile polymers and copolymers, polyolefins containing halogen (such as polyvinyl chloride and polyvinylidene chloride), fluoropolymers, ionomeric polymers, polymers containing ketone group(s), liquid crystal polymers, polyamide-imides, polymers containing olefinic double bond(s) (such as polybutadiene, polydicyclopentadiene), polyolefin copolymers, polyphenylene oxides, polysiloxanes, poly(vinyl alcohols), polyurethanes, thermoplastic elastomers, and the like.

Generally, the polymeric groups described in Volume 18 of the Encyclopedia of Chemical Technology, KIRK-OTHMER, (1982), page 328 to page 887, and Modern Plastics Encyclopedia '98, pages B-3 to B-210, and "Polymers: Structure and Properties," by C. A. Daniels, Technomic Publishing Co., Lancaster, Pa. (1989), all incorporated in their entirety herein by reference, can be used as the polymeric groups which comprise the group "polymer". These polymeric groups can be prepared in a number of ways and such ways are known to those skilled in the art. The above referenced KIRK-OTHMER section, Modem Plastics Encyclopedia, and C. A. Daniels' reference provide methods in which these polymeric groups can be prepared.

The polymeric group can be preferably a polyolefin group, a polyurethane group, a polystyrenic group, a polyacrylate group, a polyamide group, a polyester group, or mixtures thereof. Examples of R groups can be the same as previously described above. p can be 1-25, 26-50, 51-75, 76-100, 101-500, and is preferably 1 to 100, and more preferably 5 to 50.

Also, the organic group(s) attached to the pigment can be one or more types of dyes, such as, but not limited to, Nile Blue A, Toluidine Blue, Tryan Blue, C.I. Acid Blue 40, C.I. Acid Blue 129, C.I. Acid Blue 9, C.I. Acid Blue 185, C.I. Direct Blue 71, C.I. Direct Blue 199, C.I. Direct Red 9, C.I. Acid Red 18, C.I. Acid Red 27, C.I. Direct Yellow 86, C.I. Direct Yellow 4, C.I. Acid Yellow 23, and C.I. Food Black 2. Besides the organic group comprising the dye, an organic group having an ionic group and a counterionic group can have a dye serving as the counterionic group. Attaching a dye to the pigment can provide the advantage of modifying the color properties of the pigments. Also, the organic group(s) attached to the pigment can be one or more types of light stabilizers, e.g., hindered amine light stabilizer (HALS) or antioxidant.

In an embodiment of the present invention, the modified particle can be a polymer coated modified particle, such as a modified pigment product. For instance, the modified pigment is at least partially coated with one or more polymers and can be substantially or fully coated by one or more polymers. The use of the term "coated" includes partially and fully coated carbon products and modified pigment products. The polymer in this invention partially or fully encapsulates the modified pigment product, wherein the modified pigment product is the core and the polymer is the shell. The polymer(s) coated onto or used to encapsulate the modified pigment product is preferably present on the modified pigment product such that the polymer(s) is not substantially extractable by a solvent. More preferably, the polymer(s) on the modified pigment product is attached by physical (e.g., adsorption) and/or chemical means (e.g. chemical bonding, grafting).

The modified pigment product coated with a polymer can be a modified pigment product having at least one organic group attached to the pigment product. The organic group can be substituted with an ionic, ionizable, or polar group. The pigment product which has the organic group attached thereto can be any pigment product capable of having at least one organic group attached to the pigment product.

Another set of organic groups which may be attached to the pigment are organic groups having an aminophenyl, such as $(C_6H_4)$—$NH_2$, $(C_6H_4)$—$CH_2$—$(C_6H_4)$—$NH_2$, $(C_6H_4)$—$SO_2$—$(C_6H_4)$—$NH_2$. Organic groups also include aromatic sulfides, represented, for instance, by the formulas Ar—$S_n$—Ar' or Ar—$S_n$—Ar", wherein Ar and Ar' are independently arylene groups, Ar" is an aryl and n is 1 to 8.

Preferably, the organic group comprises an aromatic group and/or a $C_1$-$C_{100}$ alkyl group (and more preferably a $C_1$-$C_{12}$ alkyl group) directly attached to the particle, such as a pigment, optionally with an ionic, ionizable, or polar group.

More than one type of organic group can be attached to the particle, or two or more modified particles with different attached organic groups can be used. Using two or more different types of organic groups permits a combination of properties. If two different types of organic groups are attached, for example, a sulfanilic group and a styrenic group, the sulfanilic group promotes dispersibility and the styrenic group serves as a radical grafting site. The ratio of the different organic groups can be the same or different.

A minimum treatment level of the ionic, ionizable, or polar group can be used to impart stability to the dispersion. For example, groups such as ionic species (e.g., sulphates, phosphates, alkali salts of organic acids or quaternary ammonium salts), non-ionic species (e.g., hydroxyl, organic acids) or surfactant stabilizers (e.g., SDMS, SDS, Antarox) can be used to provide stable particle dispersions in aqueous media. Dispersion of the modified particle in organic liquids can be facilitated in a similar manner but employing treatments which are more compatible with these less polar environments. Treatment levels of the organic group for purposes of radical grafting sites would depend on material uses. For instance, attachment of epoxy groups would facilitate grafting to hydroxyl bearing polymer matrices such as polyurethanes or polycarbonates or amine matrices such as nylon. Other examples include the attachment of radical sensitive vinyl groups such as styrenics or acrylates, or methacrylates, to facilitate crosslinking type reactions in radical polymerizations.

Also, a combination of different modified particles can be used. For instance, a modified pigment having one type of organic group attached thereto can be used in combination with another modified pigment having a different organic group attached thereto. Also, a modified pigment such as an aggregate comprising a carbon phase and a silicon-containing species phase can be used in combination with a modified carbon product having an attached organic group, and so on.

The modified particle which is coated with one or more polymers can have any particle size and/or surface area so long as the particle is capable of being at least partially coated with one or more polymers. Preferably, the primary particle size of the modified pigment is from about 5 nm to about 100 nm and more preferably from about 8 nm to about 75 nm. The nitrogen surface area as measured by the BET method, of the modified carbon product is preferably from about 20 m²/g to about 1500 m²/g and more preferably from about 25 m²/g to about 700 m²/g and most preferably from about 30 m²/g to about 250 m²/g.

The thickness of the coating on the modified particle can be uniformed or can vary in thickness. The thickness of the coating can be about 1 nm or more. Preferably, the polymer coated onto the modified particle product is substantially uniform in thickness. Preferably, the thickness of the polymer coating on the modified particle is from about 10 nm to about 100 nm, more preferably from about 20 nm to about 75 nm, and most preferably from about 30 nm to about 50 nm.

The modified particle can have more than one coating or shell. In other words, the modified particle can have multiple layers of shells or coatings which partially or fully encapsulate the modified particle or a previous coating or shell. The polymers comprising the various layers can be the same or different. For instance, one layer can be cross-linked while the next layer can be not cross-linked. Each of the various coatings, if more than one is present on the modified particle, can be substantially the same or vary in thickness if desired.

The polymer which is coated onto the modified particle can be a homo-polymer, copolymer, terpolymer, and/or a polymer containing any number of different repeating units.

The polymer can be any type of polymer, such as a random polymer, alternating polymer, graft polymer, block polymer, star-like polymer, and/or comb-like polymer. The polymer can also be one or more polyblends. The polymer can be an interpenetrating polymer network (IPN); simultaneous interpenetrating polymer network (SIN); or interpenetrating elastomeric network (IEN). The polymer can be thermoplastic or thermosettable.

Specific examples of polymers include, but are not limited to, linear and non-linear polymers such as polyethylene, poly(vinylchloride), polyisobutylene, polystyrene, polycaprolactam (nylon), polyisoprene, and the like. Other general classes of polymers include polyamides, polycarbonates, polyelectrolytes, polyesters, polyethers, (polyhydroxy)benzenes, polyimides, polymers containing sulfur (such as polysulfides, (polyphenylene)sulfide, and polysulfones, polyolefins, polymethylbenzenes, polystyrene and styrene copolymers (ABS included), acetal polymers, acrylic polymers, acrylonitrile polymers and copolymers, polyolefins containing halogen (such as polyvinyl chloride and polyvinylidene chloride), fluoropolymers, ionomeric polymers, polymers containing ketone group(s), liquid crystal polymers, polyamide-imides, polymers containing olefinic double bond(s) (such as polybutadiene, polydicyclopentadiene), polyolefin copolymers, polyphenylene oxides, polyurethanes, thermoplastic elastomers, silicone polymers, alkyd, epoxy, unsaturated polyester, vinyl ester, urea-, melamine-, or phenol-formaldehyde resins, and the like. More particular examples of polymers include acrylic polymers, methacrylic polymers, or styrenic polymers.

The polymer coated modified particles can be made by a number of ways including, but are not limited to, aqueous mediated polymerization environments such as emulsion polymerization or suspension polymerization processes as well as solvent based polymerizations. The polymerizations involved are generally chain growth polymerizations and/or step growth polymerizations.

In another embodiment, the modified particle, for instance a modified pigment, has at least one organic group attached to the pigment particles and the organic group is positively chargeable. The organic group can be attached to the pigment in various amounts, i.e., low to high amounts, thus allowing fine control over charge modification. The organic group that is attached to the pigment particles can be any group which permits the modified pigment to be positively chargeable. Preferably, the organic group comprises an aromatic group or a $C_1$-$C_{20}$ alkyl group, wherein either group can be substituted or unsubstituted. It is also preferred that the aromatic group or $C_1$-$C_{20}$ alkyl group is directly attached to the pigment particles. Preferred groups of positively chargeable organic groups are nitrogen containing or phosphorus containing organic groups.

Preferred positive chargeable organic groups have the general structures:

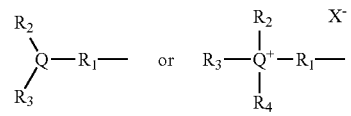

wherein Q represents the elements nitrogen or phosphorus; X represents a counterion such as $Cl^-$, $Br^-$, $ArSO_3^-$, and the like; $R_1$ represents an alkylene group or an arylene group attached to the pigment; and $R_2$, $R_3$, and $R_4$, which may be the same or different, each represent an alkyl group or an aryl group. Preferably, the alkylene or alkyl group is a $C_1$-$C_{10}$ alkylene or alkyl group and the arylene or aryl group is a $C_6$-$C_{20}$ arylene or aryl group. For the purposes of this invention, aryl and arylene groups include heteroaryl and heteroarylene groups, respectively. Other preferred organic groups that can be attached to the pigment particles include, but are not limited to the following:

| | |
|---|---|
| $(C_4H_9)NHCH_2CH_2CH_2$— | $NH_2CH_2CH_2$— |
| $(C_4H_9)_2NCH_2CH_2CH_2$— | $NH_2CH_2CH_2CH_2$— |
| $(C_8H_{17})NHCH_2CH_2CH_2$— | $NH_2CH_2CH_2CH_2CH_2$— |
| $(CH_8H_{17})_2NCH_2CH_2CH_2$— | $NH_2CH_2CH_2CH_2CH_2CH_2$— |
| $ArNHCH_2CH_2$— | $NH_2CH_2CH_2NHCH_2CH_2CH_2$— |
| $ArNHCH_2CH_2CH_2$— | $NH_2CH_2CH_2NHCH_2CH_2CH_2NHCH_2CH_2CH_2$— |
| $ArNHCH_2CH_2CH_2CH_2$— | $(CH_3)NHCH_2CH_2CH_2$— |
| $ArNHCH_2CH_2CH_2CH_2CH_2$— | $(CH_3)_2NHCH_2CH_2CH_2$— |
| $ArAr'NCH_2CH_2$— | $(C_2H_5)NHCH_2CH_2CH_2$— |
| $ArAr'NCH_2CH_2CH_2$— | $(C_2H_5)_2NCH_2CH_2CH_2$— |
| $ArAr'NCH_2CH_2CH_2CH_2$— | —$C_6H_4(NC_5H_5)^+X^-$(as defined above) |
| $ArAr'NCH_2CH_2CH_2CH_2CH_2$— | —$C_5H_4N(CH_3)^+X^-$(as defined above) |
| $NH_2CONHCH_2CH_2CH_2$— | |
| $(CH_3)HCONHCH_2CH_2CH_2$— | |
| $(CH_3)_2NCONHCH_2CH_2CH_2$— | |

-continued (C$_2$H$_5$)NHCONHCH$_2$CH$_2$CH$_2$—
(C$_2$H$_5$)$_2$NCONHCH$_2$CH$_2$CH$_2$—
(C$_4$H$_9$)NHCONHCH$_2$CH$_2$CH$_2$—
(C$_4$H$_9$)$_2$NCONHCH$_2$CH$_2$CH$_2$—
CH$_3$OCOCH$_2$CH$_2$NHCH$_2$CH$_2$CH$_2$—
(C$_2$H$_5$)OCOCH$_2$CH$_2$NHCH$_2$CH$_2$CH$_2$—
(C$_4$H$_9$)OCOCH$_2$CH$_2$NHCH$_2$CH$_2$CH$_2$—
NH$_2$Ar—
(CH$_3$)NHAr—
(CH$_3$)$_2$NAr—
NH$_2$CH$_2$Ar—
(CH$_3$)$_2$NCH$_2$Ar—
(CH$_3$)$_2$NCH$_2$CH$_2$Ar—
NH$_2$CH$_2$CH$_2$Ar—
(CH$_3$)NHCH$_2$CH$_2$Ar—
(CH$_3$)$_2$NCH$_2$CH$_2$Ar—
Cl$^-$(CH$_3$)$_3$N$^+$CH$_2$CH$_2$CH$_2$—
Cl$^-$(C$_2$H$_5$)$_3$N$^+$CH$_2$CH$_2$CH$_2$—
Cl$^-$(C$_4$H$_9$)$_3$N$^+$CH$_2$CH$_2$CH$_2$—
Cl$^-$(C$_2$H$_5$)(CH$_3$)$_2$N$^+$CH$_2$CH$_2$CH$_2$—
Cl$^-$(C$_4$H$_9$)(CH$_3$)$_2$N$^+$CH$_2$CH$_2$CH$_2$—
Cl$^-$(C$_8$H$_{17}$)(CH$_3$)$_2$N$^+$CH$_2$CH$_2$CH$_2$—
(HOCH$_2$CH$_2$)$_2$NCH$_2$CH$_2$CH$_2$—
(HOCH$_2$CH$_2$)$_2$NAr—

-Ar-SO$_2$NH(C$_4$H$_3$N$_2$)

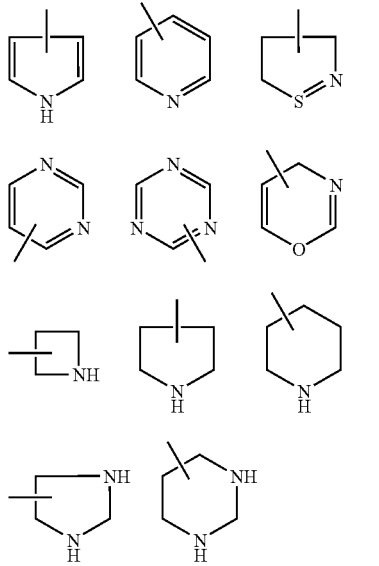

in which Ar represents an aromatic group and Ar' represents an aromatic group. The aromatic group includes, but is not limited to, unsaturated cyclic hydrocarbons containing one or more rings. The aromatic group may be substituted or unsubstituted. Aromatic groups include aryl groups (for example, phenyl, naphthyl, anthracenyl, and the like), and heteroaryl groups (imidazolyl, pyrazolyl, pyridinyl, thienyl, thiazolyl, furyl, triazinyl, indolyl, and the like). In a similar manner, negatively chargeable particles can be produced using the appropriate functional groups, such as sulfamides.

A combination of organic groups such as an organic group comprising a pyridyl group and an organic group comprising a quaternary ammonium group can be used.

As stated, the organic group is a $C_1$-$C_{100}$ alkyl group (more preferably a $C_1$-$C_{12}$ alkyl group), an aromatic group, or other organic group, monomeric group, or polymeric group, each optionally having a functional group or ionic or ionizable group. More preferably, these groups are directly attached to the particles.

The polymeric group can be any polymeric group capable of being attached to a particle. The polymeric group can be a polyolefin group, a polystyrenic group, a polyacrylate group, a polyamide group, a polyester group, or mixtures thereof. Monomeric groups are monomeric versions of the polymeric groups.

The organic group can also be an olefin group, a styrenic group, an acrylate group, an amide group, an ester, or mixtures thereof. The organic group can also be an aromatic group or an alkyl group, either group with an olefin group, a styrenic group, an acrylate group, an amide group, an ester group, or mixtures thereof, wherein preferably the aromatic group, or the alkyl group, like a $C_1$-$C_{12}$ group, is directly attached to the particle.

The polymeric group can include an aromatic group or an alkyl group, like a $C_1$-$C_{12}$ group, either group with a polyolefin group, a polystyrenic group, a polyacrylate group, a polyamide group, a polyester group, or mixtures thereof.

The organic group can also comprise an aralkyl group or alkylaryl group, which is preferably directly attached to the particle. Other examples of organic groups include a $C_1$-$C_{100}$ alkyl group, such as a $C_{20}$-$C_{60}$ alkyl group. Examples of other organic groups are organic groups having the following formulas (hyphens on one or more ends represents an attachment to a particle or to another group):

- —Ar—$CO_2(C_mH_{2m+1})$, where m=0 to about 20;
- —Ar—$(C_nH_{2n+1})$, where n=1 to about 50;
- —Ar—$C_pH_{2p}$—Ar—, where p=1 to about 10;
- —Ar—$CX_3$, where X is a halogen atom;
- —Ar—O—$CX_3$, where X is a halogen atom;
- —Ar—$SO_3^-$;
- —Ar—$SO_2(C_qH_{2q-1})$, where q=about 2 to about 10;
- —Ar—$S_2$—Ar—$NH_2$;
- —Ar—$S_2$—Ar—;
- —Ar$SO_2$H;
- —Ar—$((C_nH_{2n})COOX)_m$, where n=0 to 20, m=1 to 3, and X=H, cations, or organic group; These groups can be further activated and/or reacted with such groups as carbodiimides and further reacted with $NH_2$-terminated functionalization groups; $SOCl_2$, or $PCl_3$, or $PCl_5$ to be converted to —Ar—$(C_nH_{2n})COCl)_m$ groups and further reacted with OH-terminated functionalization groups.
- —Ar—$((C_nH_{2n})OH)_m$, where n=0 to 20, m=1 to 3; These groups can be further activated and/or reacted with such groups as tosyl chloride and subsequently reacted with amino-terminated ligands; carbonyldiimidazole and subsequently reacted with amino-terminated ligands; carbonyl-chloride terminated ligands; and epoxy terminated ligands.
- —Ar—$((C_nH_{2n})NH_2)_m$, where n=0 to 20, m=1 to 3, and its protonated form: —Ar—$((C_nH_{2n})NH_3X)_m$, where X is an ion; These groups can be further activated and/or reacted with such groups as carbodiimide activated carboxyl-terminated ligands; carbonyldiimidazole activated hydroxy-terminated ligands; tosyl activated hydroxy-terminated ligands; vinyl terminated ligands; alkylhalide terminated ligands; or epoxy terminated ligands.
- —Ar—$((C_nH_{2n})CHNH_3^+COO^-)_m$ where n=0 to 20 and m=1 to 3; These groups can be derivatized further by reaction through the carboxylic group by reaction with $NH_2$ or OH terminated groups or through the amino group by reaction with activated carboxy-terminated ligands, activated hydroxy-terminated ligands, vinyl ligands, alkylhalide terminated ligands, or epoxy terminated ligands.
- —Ar—$((C_nH_{2n})CH=CH_2)_m$, where n=0 to 20, m=1 to 3 or —Ar—$((C_nH_{2n})SO_2CH=CH_2)_m$, where n=0 to 20, m=1 to 3. These groups can be further activated and/or reacted with such groups as amino-terminated ligands; peroxy-acids to form epoxides and subsequently reacted with hydroxy- or amino-terminated ligands; hydrogen halides to form —Ar$((C_nH_{2n})CH_2CH_2X)_m$ groups and subsequently reacted with amino-terminated ligands.

Other reaction schemes can be used to form various groups onto the particles.

Other mixtures of organic groups include the following:
- —Ar—$SO_3^-$ and —Ar$(C_nH_{2n+1})$, where n=1 to about 50;
- —Ar—$S_2$—Ar—$NH_2$ and —Ar$C_pH_{2p}$Ar—, where p=1 to about 10;
- —Ar—$S_2$—Ar— and —Ar$C_pH_{2p}$Ar—, where p=1 to about 10; or
- at least two different —Ar—$CO_2(C_mH_{2m+1})$, where m=0 to about 20.

The various organic, monomeric, and polymeric groups described above and below which are part of the modified particles can be unsubstituted or substituted and can be branched or linear.

As described earlier, one or more organic groups can be attached to the particle, for example, the pigment. Further, two or more modified pigments, each having a different organic group attached to the pigment, can be used. Also, one organic group having an ionic or ionizable group can be used in connection with a second or additional organic groups with or without ionic or ionizable groups and so on. Also, combinations of pigments which differ, for example, by morphology or surface area, can be used. Treatment levels of the attached groups can be advantageously varied in order to produce a variety of different sensor performances.

As stated earlier, with respect to an embodiment of the present invention, the sensors of the present invention are a matrix of the conducting regions and the nonconducting regions. This matrix can be formed by dissolving the nonconducting materials into a solvent and introducing the modified particles into the solution containing the dissolved nonconducting materials. Many techniques including, but not limited to, solution casting, suspension casting, and mechanical mixing can fabricate the sensors of the present invention. In general, solution casting routes are advantageous because they provide homogeneous structures and are easy to process. With solution casting routes, spin, spray, or dip coating can easily fabricate resistor elements. Suspension casting still provides the possibility of spin, spray, or dip coating, but more heterogeneous structures than with solution casting are expected. With mechanical mixing, there are no solubility restrictions since it involves only the physical mixing of the resistor components, but device fabrication is more difficult since spin, spray, and dip coating are no longer possible. In certain embodiments, the sensor or chemi-resistor is deposited as a surface layer on a solid matrix that provides means for supporting the leads. Typically, the solid matrix is a chemically inert, nonconductive substrate, such as a glass or ceramic.

In more detail, and as an example, in solution casting, one or more of the components of the chemi-resistor are suspended or dissolved in a common solvent. A non-conductive material such as the non-conductive polymer is dissolved in an appropriate solvent, such as THF, acetonitrile, water, and the like. The modified pigment can then be suspended into this solution and the resulting mixture is used to dip coat electrodes. Also, mechanical mixing can be used to mix the nonconducting materials with the conducting materials such as the modified pigments. Once fabricated, the individual element forming the sensors can be optimized for a particular application by varying their chemical makeup and morphologies. The chemical nature of the chemi-resistors determines which analytes will respond in their ability to distinguish different analytes. The relative ratio of conducting to nonconducting components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalog of information on chemically diverse sensors made with varying ratios of insulating to conducting components and by differing fabrication routes, sensors can be chosen that are appropriate for the analytes expected in a particular application, their concentrations, and the desired response times. Further optimization can then be preformed in an iterative fashion as feedback on the performance of an array under particular conditions becomes available.

With respect to the above description of the manufacturing of the sensors of the present invention for certain embodiments, the embodiment wherein the sensor contains a layer having conductive modified particles and preferably no non-conducting material, these sensors can be manufactured in a similar fashion. In more detail, the modified particles used to form the layer for the sensor can be applied to a substrate such as an inert substrate in the same fashion that inks are applied to a substrate. For instance, the modified particles can be applied by printing methods known to those skilled in the art which include, but are not limited to, inkjet type printing and the like. Essentially, any means used to form a layer containing pigments or any device used to form an image on a substrate can be used for purposes of forming the layer of conductive modified particles for the sensor of the present invention. Generally, the conductive modified particles are formed into a dispersion which can be aqueous or non-aqueous and then this dispersion is applied to a substrate to form a layer wherein the non-aqueous or aqueous solvent is removed, such as by evaporation or other techniques. The dispersion containing the conductive modified particles can also contain other conventional ingredients typically used in inks or coatings such as, but not limited to, binders, additives to improve printability drying, and the like. For purposes of the present invention, the aqueous or non-aqueous solvent can also be considered an aqueous or non-aqueous vehicle.

The sensor arrays can comprise other different sensors, including, but not limited to, surface acoustic wave (SAW) sensors, quartz microbalances, organic semiconducting gas sensors, bulk conducting polymer sensors, polymeric coating on an optical fiber sensors, conducting/nonconducting region sensors and conducting filler in insulating polymer sensors, dye impregnated polymeric coatings on optical fibers, polymer composites, micro-electro-mechanical system devices, micromachined cantilevers, and micro-opto-electro-mechanical system devices.

The chemi-resistor or sensor may itself form a substrate for attaching the lead or the resistor or, the chemi-resistor can be deposited as a surface layer on a solid matrix which provides means for supporting the leads.

Sensor arrays particularly well-suited to scaled up production are fabricated using integrated circuit (IC) design technologies. For example, the resistors can easily be integrated on the front end of a simple amplifier interfaced to an A/D converter to efficiently feed the data stream directly into a neural network software or hardware analysis section. Microfabrication techniques can integrate the chemiresistors directly onto a micro-chip which contains the circuitry for analog signal conditioning/processing and then data analysis. This provides for the production of millions of incrementally different sensor elements in a single manufacturing step, for instance, using inkjet ink type technology. The sensor array of a million distinct elements only requires a one centimeter by one centimeter sized chip employing lithography at a ten micron feature level, which is within the capacity of conventional commercial processing and deposition methods. This technology permits the production of sensitive, small-size stand alone chemical sensors.

Preferred sensor arrays have a predetermined inter-sensor variation in the structure or composition of the nonconductive regions (e.g., the nonconductive organic material). The variation may be quantitative and/or qualitative. For example, the concentration of the nonconductive organic polymer in the blend can be varied across sensors. Alternatively, a variety of different organic polymers may be used in different sensors.

An electronic nose for detecting an analyte in a fluid is fabricated by electrically coupling the sensor leads of an array of compositionally different sensors to an electrical measuring device. The device measures changes in resistance at each sensor of the array, preferably simultaneously and preferably over time. Frequently, the device includes a signal processing means and is used in conjunction with a computer and data structure for comparing a given response profile to a structure-response profile database for qualitative and quantitative analysis. As such, in another embodiment, the present invention relates to a system for detecting an analyte in a fluid, comprising: a sensor array comprising at least first and second chemically sensitive resistors, each chemically sensitive resistor comprising a plurality of alternating regions comprising a nonconductive region, such as a nonconductive organic material, and conductive region, such as a modified carbon black conductive material, compositionally different than the nonconductive region. Each chemi-resistor provides an electrical path through the alternating nonconducting region and the conductive regions, a first electrical resistance when contacted with a first fluid comprising an analyte at a first concentration and a second different electrical resistance when contacted with a second fluid comprising the analyte at a second different concentration, the difference between the first electrical resistance and the second electrical resistance of the first chemically sensitive resistor being different from the difference between the first electrical resistance and the second electrical resistance of the second chemically sensitive resistor under the same conditions; an electrical measuring device electrically connected to the sensor array; and a computer comprising a resident algorithm; the electrical measuring device detecting the first and said second electrical resistances in each of said chemically sensitive resistors and the computer assembling the resistances into a sensor array response profile.

In addition, another embodiment involves a system for detecting an analyte in a fluid, which involves a sensor array containing two or more chemically sensitive resistors or sensors. At least one of the sensors contains a layer having conductive modified particles, as described above.

Typically a sensor array or electronic nose comprises at least ten, usually at least 100, and often at least 1000 different sensors, though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. The fluids may be liquid or gaseous in nature. The first and second fluids may reflect samples from two different embodiments, a change in the concentration of an analyte in a fluid sampled at two time points, a sample and a negative control, etc. The sensor array necessarily comprises sensors which respond differently to a change in an analyte concentration, i.e., the difference between the first and second electrical resistance of one sensor is different from the difference between the first and second electrical resistance of another sensor. In addition, the sensor array can comprise redundant sensors that can be advantageous for maximizing the signal and thus reducing the noise in the signal.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analytes may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

In certain aspects, the present invention provides methods for the rapid construction of large libraries of sensors through combinatorial techniques. Combinatorial chemistry is a generic term that describes a series of innovative technologies that are designed to automate and simplify the selection, synthesis, and fabrication of candidate ligands attached to the particles(s). The initial step of the combinatorial process is selection of compounds such as ligands or functional groups attached to the ligands, for inclusion in a library of compounds. In addition, highly automated sampling handling and analysis has been developed to analyze the volume of compounds in the combinatorial library.

In certain embodiments, the sensor hysteresis using the sensors containing the modified particles of the present invention is reduced or eliminated. The presence of hysteresis may affect the reproducibility of the response. As a consequence, the response is also faster with the modified sensors of the present invention. In other aspects, the sensors of the present invention are used with other polymers to increase selectivity. In this embodiment, the modified particles can be more readily dispersed in certain organic solvents.

Since the goal of the array of sensors is to produce different responses amongst two or more sensors in order to create odor signatures from the readings obtained by the electrical measuring apparatus, there are a variety of ways to have each sensor different from each other. The various variables that can be used to achieve a variety of different sensors in order to form the array for purposes of the preferred embodiment of the present invention include, but are not limited to, a) the amount of conductive modified particle forming the layer of the sensor; b) the amount of organic group, if used, attached to the conductive particles; c) using different types of organic groups, if used, that are attached to the conductive particles (e.g., using polymers of different chain lengths); d) using different conductive particles (e.g., using a carbon black having a different BET in one sensor compared to another sensor and yet treating both types of carbon blacks with the same organic group); e) using conventional sensors in combination with the sensors of the present invention; and f) using a sensor having conductive modified particles with nonconducting materials. Any one or more of these variables can be used to form a variety of different sensors in order to achieve odor signatures which can then be used to detect the concentration of an analyte and/or identify the analyte. Any means to alter the response of each of the sensors in the array in order to obtain a different response from sensor to sensor is preferred and can be used for purposes of the present invention.

The array of sensors can be formed on an integrated circuit using semiconductor technology methods, an example of which is disclosed in PCT Patent Application Serial No. WO 99/08105, entitled "Techniques and Systems for Analyte Detection," published Feb. 19, 1999, and incorporate herein by reference.

A wide variety of analytes and fluids may be analyzed by the disclosed sensors, arrays and noses so long as the subject analyte is capable of generating a differential response across a plurality of sensors of the array. Analyte applications include broad ranges of chemical classes including, but not limited to, organics such as alkanes, alkenes, alkynes, dienes, alicyclic hydrocarbons, arenes, heterocyclics, alcohols, ethers, ketones, aldehydes, carbonyls, carbanions, poly-nuclear aromatics and derivatives of such organics, e.g., halide derivatives, etc., microorganisms, fungi, bacteria, microbes, viruses, metabolites, biomolecules such as sugars, isoprenes and isoprenoids, fatty acids and derivatives, etc.

Accordingly, commercial applications of the sensors, arrays, and noses include, but are not limited to, environmental toxicology and remediation, biomedicine, materials quality control, food and agricultural products monitoring. Further applications include, but are not limited to: heavy industrial manufacturing (automotive, aircraft, etc.), such as ambient air monitoring, worker protection, emissions control, and product quality testing; oil/gas petrochemical applications, such as combustible gas detection, $H_2S$ monitoring, and hazardous leak detection and identification; emergency response and law enforcement applications, such as illegal substance detection and identification, arson investigation, hazardous spill identification, enclosed space surveying, and explosives detection; utility and power applications, such as emissions monitoring and transformer fault detection; food/beverage/agriculture applications, such as freshness detection, fruit ripening control, fermentation process monitoring and control, flavor composition and identification, product quality and identification, and refrigerant and fumigant detection; cosmetic/perfume applications, such as fragrance formulation, product quality testing, and patent protection fingerprinting; chemical/plastics/pharmaceuticals applications, such as fugitive emission identification, leak detection, solvent recovery effectiveness, perimeter monitoring, and product quality testing; hazardous waste site applications, such as fugitive emission detection and identification, leak detection and identification, and perimeter monitoring; transportation applications, such as hazardous spill monitoring, refueling operations, shipping container inspection, and diesel/gasoline/aviation fuel identification; building/residential applications, such as natural gas detection, formaldehyde detection, smoke detection, automatic ventilation control (cooking, smoking, etc.), and air intake monitoring; hospital/medical applications, such as anesthesia and sterilization gas detection, infectious disease detection, breath, wound and body fluids analysis, and telesurgey.

In yet another aspect, the present invention relates to a method for detecting the presence of an analyte in a fluid, the method comprising: resistively sensing the presence of an analyte in a fluid with a sensor comprising an array comprising at least first and second chemically sensitive resistors each comprising a plurality of alternating nonconductive regions, such as nonconductive organic material, and conductive regions, such as modified particles compositionally different than the nonconductive region, each resistor providing an electrical path through the nonconducting region and a region containing the modified particles, a first electrical resistance when contacted with a first fluid comprising an analyte at a first concentration and a second different electrical resistance when contacted with a second fluid comprising said analyte at a second different concentration.

The general method for using the disclosed sensors, arrays, and electronic noses for detecting the presence of an analyte in a fluid involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

The modified particles used in the sensors of the present application provide numerous advantages over conventional sensors. For instance, the sensors containing the modified particles can be more sensitive to analytes than conventional sensors using unmodified carbon black. This ability to be highly sensitive to analytes can lead to greater changes in resistance, thus leading to a better discrimination value between various sensors. Furthermore, the present invention provides the ability for the sensor to provide faster response times upon exposure of the sensor to an analyte. In addition, the sensors of the present invention provide highly linear relationships to concentrations of the analyte, temperature, and humidity conditions. This can be important with respect to providing sensors that respond consistently and predictably to variances that occur with respect to these conditions. In addition, the modified particles used in the sensors of the present application permit the formation of various dispersions which suspend the modified particles uniformly which then leads to a uniform formation of a layer containing a uniform dispersion of the modified particle thus leading to a better response when the sensor is exposed to a variety of analytes. Also, with the modified particles used in the sensors of the present invention, a one step spraying process for the manufacturing of the sensors can be achieved due to the excellent suspension and dispersion of the modified particles in the solvent which eventually is sprayed to form the sensor surface of the present invention.

Also, as described above and in the examples, the ability of the sensors using the modified particles of the present invention do lead to excellent discrimination power for a variety of analytes thus providing sensors which can properly and accurately detect analytes and/or the concentration of the analytes.

The following patents and publications provide examples of components of sensors that may be incorporated into the embodiments of the present invention: Zaromb, S., et al., "Theoretical basis for identification and measurement of air contaminants using an array of sensors having partly overlapping selectivities," *Sensors and Actuators*, 6:225-243 (1984); Stetter, et al., "Detection of hazardous gases and vapors: Pattern recognition analysis of data from an electrochemical sensor array," *Anal. Chem.*, 58:860-866 (1986); Shurmer, H. V., et al., "An electronic nose: A sensitive and discriminating substitute for a mammalian olfactory system," *IEE PROCEEDINGS*, 137, pt. G, No. 3:197-204 (June 1990); Bartlett, P. N., et al., "Electrochemical deposition of conducting polymers onto electronic substrates for sensor applications," *Sensors and Actuators*, A21-A23:911-914 (1990); Stetter, et al., "Sensor array and catalytic filament for chemical analysis of vapors and mixtures," *Sensors and Actuators* B1, 43-47 (1990); Persaud, K. C., "Odour detection using sensor arrays," *Analytical Proceedings*, 28:339-341 (10/91); Gardner, J. W., et al., "Detection of vapours and odours from a multisensor array using pattern recognition Part 1. Principal component and cluster analysis," *Sensors and Actuators B*, 4:109-115 (1991); Shurmer, H. V., et al., "Odour discrimination with an electronic nose," *Sensors and Actuators G.*, 8:11 (1992); Grate, J. W., et al., "Smart sensor system for trace organophosphorus and organosulfur vapor detection employing a temperature-controlled array of surface acoustic wave sensors, automated sample preconcentration, and pattern recognition," *Anal. Chem.*, 65:1868-1881 (1993); and Pearce, T. C., et al., "Electronic nose for monitoring the flavour of beers," *Analyst*, 118:371-377 (1993); Longergan, et al., "Array-Based Vapor Sensing Using Chemically Sensitive, Carbon Black-Polymer Resistors," *Chem. Mater.*, (1996), Vol. 8, pp. 2298-2312; Severin et al., "An Investigation of the Concentration Dependence and Response to Analyte Mixtures of Carbon Black/Insulating Organic Polymer Composite Vapor Detectors," *Anal. Chem.* 2000, 72, pp. 658-668; Snow et al., "Size-Induced Metal to Semiconductor Transition in a Stabilized Gold Cluster Ensemble," Chemistry of Materials, Vol. 10, No. 4, (1998), pp. 947-949; Talik, et al., "Sensing Properties of the CB-PCV Composites for Chlorinated Hydrocarbon Vapours," *Journal of Materials Science*, 27 (1992) pp. 6807-6810, and U.S. Pat. Nos. 5,571,401 and 5,788,833.

The present invention will be further clarified by the following examples, which are intended to be exemplary of the present invention.

EXAMPLES

Example 1

Modified carbon blacks were evaluated and compared to both standard and commercially dispersed carbon blacks. The carbon blacks were modified with a variety of functional groups such that a range of polarities were covered. Several of the carbon blacks were also treated at various levels of modification. The standard carbon blacks used in this experiment were Black Pearl 2000 (BP2000), N990, Vulcan XC72, and Columbian Conductex 975. The commercially dispersed carbon blacks were the Borden co-dispersion (Columbian Conductex 975 in toluene) and Permblak 2940 (BP2000 in water). Table I shows the various carbon blacks used as chemiresistor sensors and the solvent used to prepare the dispersion.

The sensors' performance was evaluated by exposing them to a number of analytes, most of them solvents. These analytes were chosen based on their solubility parameter to span a large "solvent space". Isobutyric acid was also chosen as a bacteria metabolic product. The solvent space can be described in terms of the solubility parameter whose values for virtually all solvents range between that of

TABLE I

Description of carbon blacks used in sensor evaluation study

| Substrate ID | Description | Solvent |
|---|---|---|
| | Standard Carbon Blacks | |
| 222 | BP2000 | Benzene |
| 223 | N990 | DMF |
| 224 | Vulcan XC72 | THF |
| 225 | Columbian Conductex 975 | Toluene |
| | Commercially Dispersed Carbon Blacks | |
| 251 | Borden Co-dispersion | Toluene |
| 252 | Permblak 2940 | Water |
| | Surface Modified Carbon Blacks | |
| 230 | oligoether-modified M700 | Ethanol |
| 231 | sulfanilic acid modified Elftex TP treated with C18 cationic amine- | Dodecane |
| 232 | trifluormethylaniline-modified Vulcan XC-72 (0.12 mmoles/gr treatment level) | Ethanol |
| 233 | trifluormethylaniline-modified Vulcan XC-72 (0.5 mmoles/gr treatment level) | Ethanol |
| 234 | butylaniline-modified Vulcan 7H (0.48 mmoles/gr treatment level) | Toluene |
| 235 | butylaniline-modified Vulcan 7H (0.12 mmoles/gr treatment level) | Toluene |
| 236 | ethyl aminobenzoate-modified Vulcan 7H (0.48 mmoles/gr treatment level) | Ethanol |
| 237 | ethyl aminobenzoate-modified Vulcan 7H (0.12 mmoles/gr treatment level) | Ethanol |
| 238 | trifluoromethylaniline-modified Vulcan 7H (0.48 mmoles/gr treatment level) | Ethanol |

TABLE I-continued

Description of carbon blacks used in sensor evaluation study

| Substrate ID | Description | Solvent |
|---|---|---|
| 239 | trifluoromethylaniline-mdoified Vulcan 7H (0.12 mmoles/gr treatment level) | Ethanol |
| 240 | aminophenylsulfatoethylsulfone-modified CSX-557 | IPA |
| 241 | Emperor S90B | IPA |
| 242 | 6 wt % coating of poly(chloromethylstyrene) on Vulcan 7H | THF |
| 243 | 24 wt % coating of poly(chloromethylstyrene) on Vulcan 7H | THF |
| 244 | 45 wt % coating of poly(chloromethylstyrene) on Vulcan 7H | THF |
| 245 | 20 wt % poly(alkylacrylate) on Sterling 4620 | THF |
| 246 | ethyl aminobenzoate-modified CSX-98 | THF |
| 247 | p-aminobenzoate and bis-trifluoromethylaniline-modified M700 | THF |
| 248 | p-aminobenzoate and aminododecanoic acid-modified M700 | Toluene |
| 249 | p-aminobenzoate and aminododecanoic acid-modified M700 | Toluene |
| 250 | p-aminobenzoic acid-modified M700 (0.8 mmoles/gr treatment level | Water |

Carbon black dispersions could not be sprayed to a measurable base resistance at these concentrations. isooctane (14) and water (48 Mpa1/2). The solubility parameter for solvents, as described by Hildebrand, can be determined from their molar energies or enthalpies of vaporization. The Hildebrand parameter is related to the cohesive energy (i.e. the attractive strength) of the molecules. In general, the larger the size of the molecule the higher the cohesive energy. Table II, shows the solubility parameter for the analytes used to evaluate the sensors' response.

TABLE II

Hildebrand solubility parameter, partition coefficient between water and octanol, and saturated (equilibrium) vapor pressure at 25° C. for solvents used as analytes in the evaluation of carbon blacks chemiresistor sensors.

| Solvent | Solubility Parameter $(MPa)^{1/2}$ | Saturated vapor Pressure @ 25° C. (kPa) |
|---|---|---|
| Dodecane | 16.2 | 0.016 |
| Toluene | 18.2 | 3.79 |
| Ethyl acetate | 18.6 | 12.60 |
| Methyl ethyl ketone | 19 | 12.60 |
| Tetrahydrofuran | 19.5 | 21.60 |
| Methylene chloride | 19.8 | 4.77 |
| Dimethyl sulfoxide | 24.6 | 0.431 |
| Ethanol | 26 | 7.87 |
| Methanol | 29.3 | 16.90 |
| Water | 48 | 2.80 |

All dispersions were made at a concentration of 0.75 wt % based on the total weight of the solvent. The solvent was chosen based on the chemical functionality of the carbon black. The carbon black was added to the appropriate solvent and sonicated for ten minutes on speed four at 15° C. using a Misonix XL2020 ultrasonic processor. After ten minutes the ultrasonic processor was paused, the dispersion was removed, shaken by hand, and then replaced for an additional ten minutes. For a complete list of the carbon black and solvent combinations used please refer to Table I.

All carbon blacks were deposited using the Iwata HP-BC airbrush onto the GASS-7100A substrates. The same dispersion was sprayed on all eight sensors using circle masks with adhesive backing. The dispersions were sprayed until the measured resistance was in the kilo-ohm range or (if this was not possible) sprayed until the resistance level could be measured by the Keithley 2002 multimeter.

All substrates were post processed for one hour at room temperature at full vacuum (<30 in. Hg) immediately following deposition and removal of the masks.

The sensor arrays were exposed to the eight analytes at the following concentrations (concentrations were calculated by dividing the saturated vapor concentration by the dilution factor, 20):

| ANALYTE | CONCENTRATION (PPM) |
|---|---|
| DMSO | 39 |
| Dodecane | 8 |
| Ethyl Acetate | 6216 |
| Ethanol | 3882 |
| Isobutyric Acid | 1993 |
| MEK | 6216 |
| THF | 10655 |
| Toluene | 1870 |

*The substrate temperatures were maintained at 28° C. and the flow rate was 400 cc/min (the sample chamber contains four sub chambers allowing for the testing of four substrates at the same time).

Figure 1:
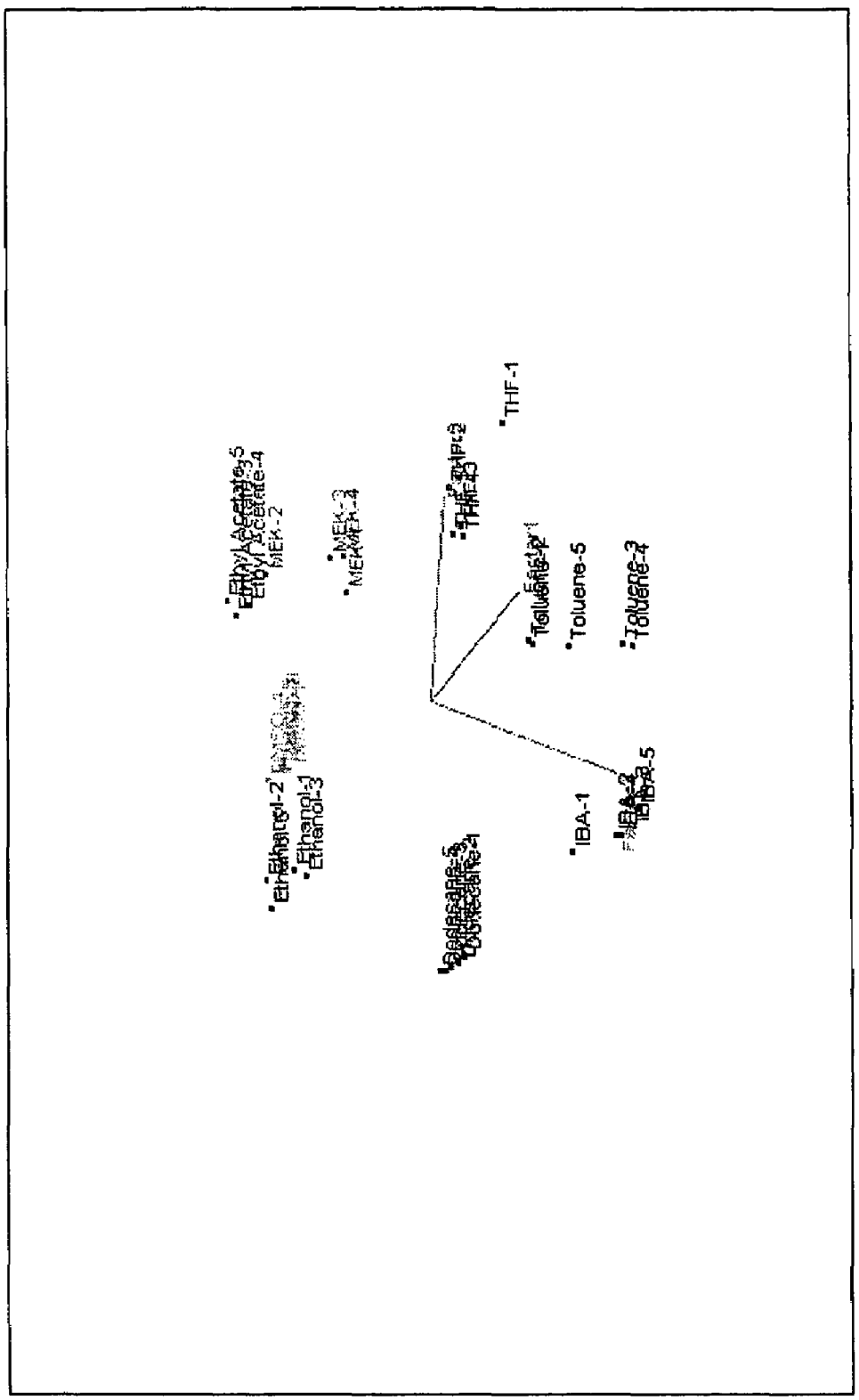
FIG. 1 is a plot obtained from a principle component analysis applied to the response of modified carbon blacks to a variety of analytes.

The temporal response of resistance vs. time for the sensor array as they are exposed to various vapors was analyzed using an IGOR program which is commercially available. Only one feature extraction of the temporal response was done and it is termed baseline correction. The baseline correction method gives a fractional difference, that is, $(R_{max}-R_{min})/R_{min}$. This technique works best for sensors that reach equilibrium. Since no other pre-processing algorithm was used, an assumption was made that all the sensors had reached equilibrium. Principal component analysis (PCA) was applied to the response data for eight analytes from the modified carbon blacks only, and this is shown in FIG. 1 (autoscaled, and normalized −1 norm in Pirouette, a commercial software by Infometrics). An outlier diagnostics was done and it indicated that 2 EA, 1 EtOH and 1 MEK where outliers and hence where removed from the plot.

Soft independent modeling of class analogy (SIMCA), was also done on this data and the off-diagonal average interclass distance (ICD) was 77.72 (Table IV).

TABLE IV

Interclass distance after application of SIMCA

|  | DMSO | DOD | EA | EtOH | IBA | MEK | THF | TOL |
|---|---|---|---|---|---|---|---|---|
| DMSO | 0.000 | 34.64 | 83.19 | 36.35 | 92.30 | 57.32 | 74.05 | 32.29 |
| DOD | 34.64 | 0.00 | 48.59 | 75.07 | 95.87 | 42.70 | 41.78 | 32.99 |
| EA | 83.19 | 48.59 | 0.00 | 271.26 | 51.07 | 7.79 | 18.04 | 10.06 |

TABLE IV-continued

Interclass distance after application of SIMCA

|      | DMSO  | DOD   | EA     | EtOH   | IBA    | MEK    | THF    | TOL    |
|------|-------|-------|--------|--------|--------|--------|--------|--------|
| EtOH | 36.35 | 75.07 | 271.26 | 0.00   | 217.09 | 234.01 | 213.73 | 102.22 |
| IBA  | 92.30 | 95.87 | 51.07  | 217.09 | 0.00   | 41.69  | 51.97  | 44.19  |
| MEK  | 57.32 | 42.70 | 7.79   | 234.01 | 41.69  | 0.00   | 11.47  | 8.026  |
| THF  | 74.05 | 41.78 | 18.04  | 213.73 | 51.97  | 11.47  | 0.00   | 6.31   |
| TOL  | 32.29 | 32.99 | 10.06  | 102.22 | 44.19  | 8.03   | 6.31   | 0.00   |

*Where DMSO is dimethyl sulfoxide; DOD is dodecan; EA is ethyl acetate; EtOH is ethanol; IBA is isobutyric acid; MEK is methyl ethyl ketone; THF is tetrahydrofuran; TOL is toluene.

TABLE V

Interclass residuals after application of SIMCA

|      | DMSO  | DOD   | EA    | EtOH   | IBA   | MEK   | THF   | TOL   |
|------|-------|-------|-------|--------|-------|-------|-------|-------|
| DMSO | 0.617 | 15.09 | 21.22 | 18.17  | 38.01 | 15.25 | 4.084 | 7.63  |
| DOD  | 25.95 | 0.57  | 57.06 | 45.59  | 49.01 | 23.62 | 5.12  | 12.78 |
| EA   | 35.90 | 22.24 | 0.931 | 31.05  | 36.19 | 5.32  | 4.26  | 4.34  |
| EtOH | 16.77 | 25.77 | 19.36 | 0.521  | 30.80 | 10.11 | 6.52  | 10.76 |
| IBA  | 70.31 | 63.20 | 62.45 | 176.01 | 0.594 | 6.48  | 8.46  | 6.55  |
| MEK  | 41.46 | 25.91 | 20.00 | 94.01  | 28.86 | 0.506 | 3.586 | 4.48  |
| THF  | 50.20 | 26.50 | 18.27 | 111.32 | 33.39 | 4.40  | 0.264 | 4.49  |
| TOL  | 28.07 | 25.66 | 23.33 | 94.44  | 38.22 | 10.48 | 2.02  | 0.619 |

Good discrimination among analytes is achieved with ICD's of 6. Overlap is a likely outcome for values less than 3. As can be seen, the interclass distances are very large for the modified carbon blacks, showing very good discrimination.

Figure 2:
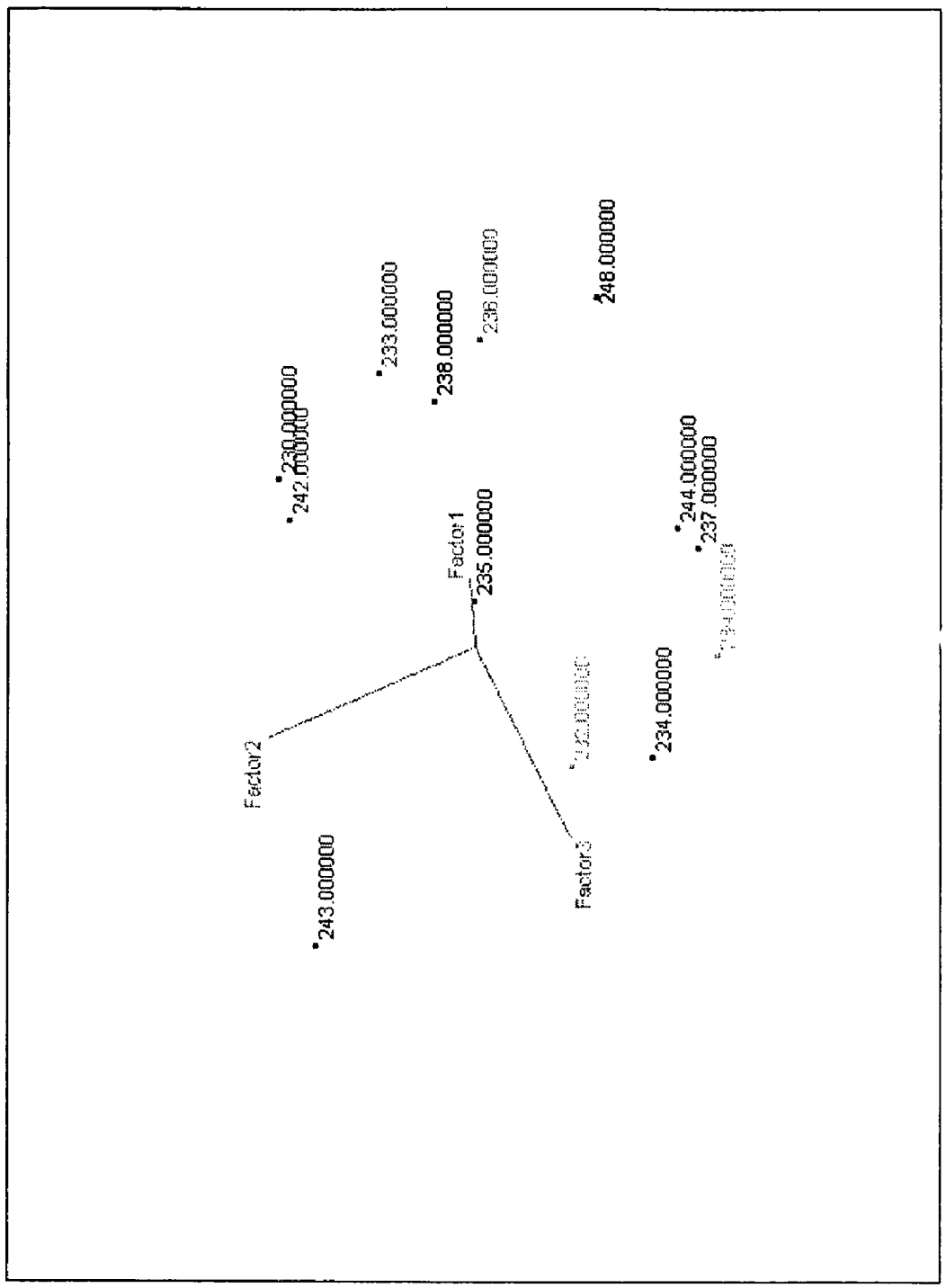
FIG. 2 is a loadings plot of principal component analysis results of sensors' responses.

An indication of the sensors' orthogonality can be inferred from a loadings plot. A loadings plot determines which variables (sensors) are important for describing the variation in the original data set. The loadings are the cosine of the angle between the principal component (PC) and the original variables. They describe how the original measurement variables relate to each of the new PC axes. As the loadings approach 1 or −1 the angle between the PC and the variables approaches 0 or 180 degrees, which means that the variable contributes much variation to the PC.[2] In the loadings plot where much of the variance is described by the first three PC's sensors maximum orthogonality is observed when the sensors form a perfect circle. FIG. 2, shows a loadings plot of PCA results. The loadings plot shows that even with the limited representation of chemical functionality on the modified carbon blacks, the discrimination power is still evenly distributed in a three-dimensional space. Hence, the reason for the large ICD's.

Figure 3:
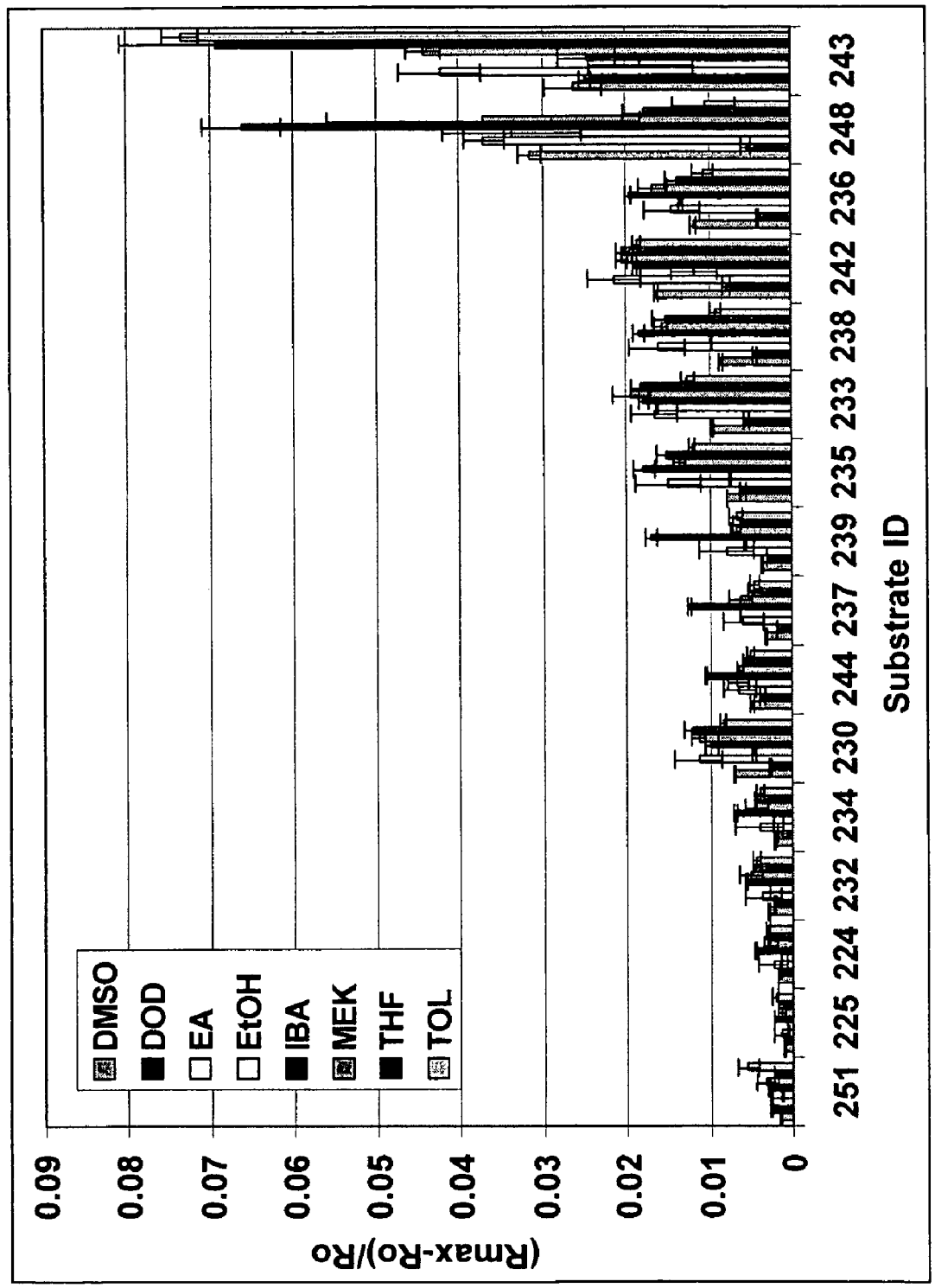
FIG. 3 is a graph showing the response of a sensor array to various analytes.

FIG. 3, shows the average (of all the exposures and for the same sensor across a substrate) fractional difference response for the sensor array to eight analytes, which was obtained using the VGS. Note, that the standard deviation is small. Tables VI-IX, show the average response for forty responses (eight sensors times five exposures each) and the response percent coefficient of variation (standard deviation divided by average, multiplied by 100) of exposure one through exposure five. Substrates 222, 246, and 247 yielded indistinguishable noisy responses and therefore, are not included in the tables. Note that the percent coefficient of variance is reasonably small for most of the responses.

The data shows that the commercially dispersed carbon black (substrate ID 251, Borden Co-dispersion—one of the controls) yields much lower response values to all analytes tested. Relative to the carbon blacks that gave the largest responses, the difference in response for substrate ID 251 ranged between 9.5 times smaller for dodecane and 31.6 times smaller for THF.

The data also shows that the response values for the other commercially dispersed carbon black (substrate ID 252, Permblak 2940) and the standard carbon blacks (substrate ID 224, Vulcan XC72 and substrate ID 225, Columbian Conductex 975) ranked in the bottom four except in the cases of DMSO and ethanol where substrate ID 252 ranked tenth and twelfth respectively. The modified carbon blacks always produced larger response values than the unmodified carbon blacks.

Example 2

The performance of a polymer composite sensor array (SS 605) was used to compare to the response of the CB sensor array without the controls (ID 222-225, 251 and 252, Table I)—that is, modified carbon blacks only. Table XIX, shows the average response of the array to temperature and humidity and Table XX, shows the response time and SN ratio. Note, that the average performance to humidity and temperature are fairly similar for both arrays. SS 605 performs better in terms of the response time and SN ratio.

TABLE XIX

Comparison of the performance of SS 605 to CB sensors

|  | TC (PPM/C.) | Average CC (Temp) | Average (R − Ro)/Ro @ 25° C. | Average (R − Ro)/Ro @ 31° C. | Average (R − Ro)/Ro @ 34° C. | Average RH sensitivity (PPM/% RH) | Average CC (for RH response) |
|---|---|---|---|---|---|---|---|
| SS 605 |  |  |  |  |  | 314 | 0.988 |
| Toluene | −308 | 0.923 | 8.68E−03 | 6.83E−03 | 5.96E−03 |  |  |
| Methanol | −131 | 0.850 | 3.23E−03 | 2.56E−03 | 2.02E−03 |  |  |
| MeCl | −26 | 0.137 | 1.64E−03 | 1.15E−03 | 1.16E−03 |  |  |
| MEK | −305 | 0.640 | 5.47E−03 | 4.11E−03 | 3.21E−03 |  |  |
| CPS without carbon black controls |  |  |  |  |  | 1050 | 0.978 |
| Toluene | −440 | 0.960 | 9.93E−03 | 6.82E−03 | 6.10E−03 |  |  |
| Methanol | −403 | 0.927 | 7.22E−03 | 5.08E−03 | 3.53E−03 |  |  |
| MeCl | −433 | 0.730 | 1.71E−03 | 1.49E−03 | 1.35E−03 |  |  |
| MEK | −344 | 0.982 | 8.68E−03 | 6.42E−03 | 5.63E−03 |  |  |
| CPS with carbon black controls |  |  |  |  |  | 763 | 0.925 |
| Toluene | −335 | 0.934 | 7.51E−03 | 5.15E−03 | 4.57E−03 |  |  |
| Methanol | −276 | 0.832 | 5.29E−03 | 3.83E−03 | 2.75E−03 |  |  |
| MeCl | −58 | 0.740 | 1.74E−03 | 1.45E−03 | 1.22E−03 |  |  |
| MEK | −265 | 0.957 | 6.53E−03 | 4.80E−03 | 4.18E−03 |  |  |

Where TC is the temperature coefficient and CC is the correlation coefficient.

TABLE XX

Comparison of response time and signal-to-noise ratio For SS 605 and CB sensors

|  | Average response time in sec. @ 31° C. | % CV of (R − Ro)/Ro @31° C. | Average SNR @ 25° C. | Average SNR @ 31° C. | Average SNR @ 34° C. |
|---|---|---|---|---|---|
| SS 605 |  |  |  |  |  |
| Toluene | 52.10 |  | 304.70 | 220.38 | 188.56 |
| Methanol | 25.37 |  | 115.27 | 86.02 | 59.47 |
| MeCl | 20.11 |  | 56.63 | 40.40 | 31.67 |
| MEK | 30.66 |  | 204.05 | 143.31 | 105.07 |
| CPS without carbon black controls |  |  |  |  |  |
| Toluene | 101.95 | 15.02 | 187.60 | 100.18 | 89.27 |
| Methanol | 77.24 | 16.52 | 154.72 | 88.21 | 75.23 |
| MeCl | 32.52 | 15.23 | 24.79 | 16.71 | 14.28 |
| MEK | 76.69 | 16.82 | 153.72 | 89.14 | 71.18 |
| CPS with carbon black controls |  |  |  |  |  |
| Toluene | 236.64 | 17.53 | 183.59 | 107.84 | 91.20 |
| Methanol | 223.73 | 15.55 | 135.43 | 82.18 | 66.65 |
| MeCl | 186.95 | 15.66 | 26.72 | 17.35 | 14.10 |
| MEK | 213.83 | 16.69 | 146.14 | 84.29 | 64.65 |

All publications, patents and patent applications mentioned in this application are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A sensor for detecting an analyte in a fluid, wherein said sensor comprises a layer comprising conductive modified particles, wherein the layer comprising conductive modified particles has a preexisting resistance that is altered in the presence of the analyte, wherein said conductive modified particles comprise carbon products or colored pigments having at least one organic group covalently bonded to the particles, wherein the sensor includes an electrical measuring apparatus electrically connected to the layer comprising conductive modified particles that detects an alteration in the preexisting resistance of the layer in the presence of the analyte, and wherein said conductive modified particles comprise an aggregate comprising a carbon phase and a silicon-containing species phase, wherein said aggregate optionally has attached at least one organic group.

2. The sensor of claim 1, wherein said organic group comprises at least one aromatic group, at least one $C_1$-$C_{100}$ alkyl group, or mixtures thereof.

3. The sensor of claim 1, wherein said organic group comprises a polymeric group.

4. The sensor of claim 1, wherein said organic group further comprises at least one ionic group, ionizable group, or both.

5. The sensor of claim 1, wherein said organic group comprises a polymer, an alkane, an alkene, an alkyne, a diene, an alicyclic hydrocarbon, an arene, a heterocyclic, an alcohol, an ether, a ketone, an aldehyde, a carbonyl, a carbanion, a polynuclear aromatic or a derivative of organic, functional group, a chiral group, a polyethylene glycol, a surfactant, a detergent, a biomolecule, a polysaccharide, a protein complex, a polypeptide, a dendrimeric material, an oligonucleotide, a fluorescent moiety, or radioactive group.

6. The sensor of claim 1, wherein said organic group comprises a 18-carbon alkyl group, a 4-carbon alkyl group, an alkyl ester, an oligoether, an anionic group, a poly(chloromethylstyrene), or a poly(alkylacrylate).

7. The array of sensors according to claim 1, wherein said sensor array comprises two or more sensors for detecting an analyte in a fluid, wherein at least at least one of the sensors comprises the sensor of claim 1, and wherein each sensor provides a different response for the same analyte with a detector that is operatively associated with each sensor.

8. The array of sensors according to claim 1, wherein said sensor array comprises two or more sensors for detecting an analyte in a fluid, wherein at least at least one of the sensors comprises the sensor of claim 1, and wherein at least two sensors each comprise a layer comprising conductive modified particles, wherein the conductive modified particles for each sensor are different from each other.

9. The sensor according to claim 1, wherein the at least one organic group directly attached to the particles is of the chemical form —X-Sp-[A]$_p$-R where X is attached to the particle and represents an aromatic or alkyl group, Sp is a spacer group, A is an alkylene oxide or polymer and R is a terminal group.

10. The sensor according to claim 1, wherein conductivity between the conductive modified particles within the layer changes due primarily to particle-to-particle distance changes between the conductive modified particles within the layer when the analyte is introduced to the sensor, and wherein the preexisting resistance of the layer changes accordingly.

11. The sensor according to claim 1, wherein the organic group is selected from the group consisting of: —$C_6H_4$—$COO^-X^+$, —$C_6H_4$—$SO_3^-X^+$, —$C_6H_4$—$(PO_3)^{-2}2X^+$, —$C_6H_2$—$(COO^-X^+)_3$, —$C_6H_3$—$(COO^-X^+)_2$, —$(CH_2)_z$—$(COO^-X^+)$, —$C_6H_4$—$(CH_2)_z$—$(COO^-X^+)$, wherein X+ is a caton selected from the group consisting of $Na^+$, $H^+$, $K^+$, $NH_4^+$, $Li^+$, $Ca_2^+$, and $Mg^+$, and z is an integer between 1 and 18 inclusive.

12. The sensor according to claim 1, wherein the alteration in the preexisting resistance of the layer in the presence of the analyte is a result of swelling of the layer comprising conductive modified particles.

13. An array of sensors for detecting an analyte in a fluid, said sensor array comprising:
a first and a second sensor electrically connected to an electrical measuring apparatus, wherein said first sensor comprises a region of nonconducting material and a region comprising conductive modified particles; and an electrical path through said region of nonconducting material and said region comprising conductive modified particles, wherein the region of nonconducting material and the region comprising conductive modified particles have a preexisting resistance that is altered in the presence of the analyte, wherein said conductive modified particles comprise carbon products or colored pigments having at least one organic group covalently bonded to the particles, aggregates comprising a carbon phase and a silicon-containing species phase and optionally having attached at least one organic group, aggregates comprising a carbon phase and metal-containing species phase optionally having attached at least one organic group, silica-coated carbon blacks, or combinations thereof and wherein the electrical measuring apparatus detects an alteration in the preexisting resistance in the presence of the analyte,
wherein said conductive modified particles comprise an aggregate comprising a carbon phase and a silicon-containing species phase, wherein said aggregate optionally has attached at least one organic group.

14. The array of sensors according to claim 13, wherein said second sensor is selected from a surface acoustic wave (SAW) sensor, a quartz microbalance, an organic semiconducting gas sensor, a bulk conducting polymer sensor, a polymeric coating on an optical fiber sensor, conducting/nonconducting regions sensor conducting filler in insulating polymer sensors, dye impregnated polymeric coating on an optical fiber, a polymer composite, a micro-electro-mechanical system device, a micromachined cantilever, or a micro-optoelectromechanical system device.

15. The array of sensors according to claim 13, wherein said organic group comprises at least one aromatic group, at least one $C_1$-$C_{100}$ alkyl group, or mixtures thereof.

16. The array of sensors according to claim 13, wherein said organic group comprises a polymeric group.

17. The array of sensors according to claim 13, wherein said organic group further comprises at least one ionic group, ionizable group, or both.

18. The array of sensors according to claim 13, wherein said organic group comprises a polymer, an alkane, an alkene, an alkyne, a diene, an alicyclic hydrocarbon, an arene, a heterocyclic, an alcohol, an ether, a ketone, an aldehyde, a carbonyl, a carbanion, a polynuclear aromatic or a derivative of organic, functional group, a chiral group, a polyethylene glycol, a surfactant, a detergent, a biomolecule, a polysaccharide, a protein complex, a polypeptide, a dendrimeric material, an oligonucleotide, a fluorescent moiety, or radioactive group.

19. The array of sensors according to claim 13, wherein said organic group comprises a 18-carbon alkyl group, a 4-carbon alkyl group, an alkyl ester, an oligoether, an anionic group, a poly(chloro-methylstyrene), or a poly(alkylacrylate).

20. The array of sensors according to claim 13, wherein the alteration in the preexisting resistance of the layer in the presence of the analyte is a result of swelling of the layer comprising conductive modified particles.

21. A sensor for detecting an analyte in a fluid, wherein said sensor comprises a layer comprising conductive modified particles, wherein the layer comprising conductive modified particles has a preexisting resistance that is altered in the presence of the analyte, wherein said conductive modified particles comprise carbon products or colored pigments having at least one organic group directly attached to the particles,
wherein the sensor includes an electrical measuring apparatus electrically connected to the layer comprising conductive modified particles that detects a change in the preexisting resistance of the layer in the presence of the analyte, and wherein the change in the preexisting resistance is due to a change in the electrical properties across more than one of the conductive modified particles within the layer, wherein each of the conductive modified particles is an aggregate comprising a carbon phase and a silicon-containing species phase having attached at least one organic group.

22. The sensor according to claim 21, wherein the at least one organic group is covalently attached to the particles.

23. The sensor according to claim 21, wherein the at least one organic group directly attached to the particles is of the chemical form —X-Sp-$[A]_p$-R where X is attached to the particle and represents an aromatic or alkyl group, Sp is a spacer group, A is an alkylene oxide or polymer and R is a terminal group.

24. The sensor according to claim 21, wherein the organic group is selected from the group consisting of: —$C_6H_4$—$COO^-X^+$, —$C_6H_4$—$SO_3^-X^+$, —$C_6H_4$—$(PO_3)^{-2}2X^+$, —$C_6H_2$—$(COO^-X^+)_3$, —$C_6H_3$—$(COO^-X^+)_2$, —$(CH_2)_z$—$(COO^-X^+)$, —$C_6H_4$—$(CH_2)_z$—$(COO^-X^+)$, wherein $X^+$ is a caton selected from the group consisting of $Na^+$, $H^+$, $K^+$, $NH_4^+$, $Li^+$, $Ca_2^+$, and $Mg^+$, and z is an integer between 1 and 18 inclusive.

25. A method for detecting the presence of an analyte in a fluid, said method comprising:

providing a sensor array comprising at least two sensors, wherein at least one sensor comprises a layer comprising conductive modified particles wherein the layer comprising conductive modified particles has a preexisting resistance that is altered in the presence of the analyte and wherein the at least one sensor includes an electrical measuring apparatus electrically connected to the layer comprising conductive modified particles that detects an alteration in the preexisting resistance of the layer in the presence of the analyte;

each sensor having an electrical path through the sensor;

contacting said sensor array with said analyte to generate a response; and detecting said response with a detector that is operatively associated with each sensor, and thereby detecting the presence of said analyte, wherein said conductive modified particles comprise carbon products or colored pigments having at least one organic group directly attached to the particles, wherein the change in the preexisting resistance is due to a change in the electrical properties across more than one of the conductive modified particles within the layer, wherein each of the conductive modified particles is an aggregate comprising a carbon phase and a silicon-containing species phase having attached at least one organic group.

26. The method according to claim 25, wherein the at least one organic group is covalently attached to the particles.

27. The method according to claim 25, wherein the at least one organic group directly attached to the particles is of the chemical form —X-Sp-$[A]_p$-R where X is attached to the particle and represents an aromatic or alkyl group, Sp is a spacer group, A is an alkylene oxide or polymer and R is a terminal group.

28. The method according to claim 25, wherein the organic group is selected from the group consisting of: —$C_6H_4$—$COO^-X^+$, —$C_6H_4$—$SO3^-X^+$, —$C_6H_4$—$(PO_3)^{-2}2X^+$, —$C_6H_2$—$(COO^-X^+)_3$, —$C_6H_3$—$(COO^-X^+)_2$, —$(CH_2)_z$—$(COO^-X^+)$, —$C_6H_4$—$(CH_2)_z$—$(COO^-X^+)$, wherein X+ is a caton selected from the group consisting of $Na^+$, $H^+$, $K^+$, $NH_4^+$, $Li^+$, $Ca_2^+$, and $Mg^+$, and z is an integer between 1 and 18 inclusive.

29. The method according to claim 25, wherein the change in the preexisting resistance of the layer is due to a changed separation distance between adjacently-positioned ones of the conductive modified particles within the layer, caused by swelling of the layer.

* * * * *